US010993772B2

(12) United States Patent
Itkowitz et al.

(10) Patent No.: US 10,993,772 B2
(45) Date of Patent: May 4, 2021

(54) SYSTEM AND METHOD FOR INTEGRATED TABLE MOTION

(71) Applicant: INTUITIVE SURGICAL OPERATIONS, INC., Sunnyvale, CA (US)

(72) Inventors: Brandon D. Itkowitz, San Jose, CA (US); Paul G. Griffiths, Santa Clara, CA (US); Jason Hemphill, Los Gatos, CA (US); Goran A. Lynch, Oakland, CA (US); Daniel N. Miller, Los Gatos, CA (US); Patrick O'Grady, Alameda, CA (US); Nitish Swarup, Sunnyvale, CA (US); Kamyar Ziaei, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 276 days.

(21) Appl. No.: 16/242,750

(22) Filed: Jan. 8, 2019

(65) Prior Publication Data
US 2019/0142533 A1 May 16, 2019

Related U.S. Application Data

(63) Continuation of application No. 15/522,169, filed as application No. PCT/US2015/057656 on Oct. 27, 2015, now Pat. No. 10,226,306.
(Continued)

(51) Int. Cl.
G06F 17/00 (2019.01)
A61B 34/30 (2016.01)
(Continued)

(52) U.S. Cl.
CPC .............. *A61B 34/30* (2016.02); *A61B 34/25* (2016.02); *A61G 13/02* (2013.01)

(58) Field of Classification Search
CPC .......... A61B 34/30; A61B 34/25; A61G 13/02
(Continued)

(56) References Cited

U.S. PATENT DOCUMENTS 4,625,837 A 12/1986 Zimmer et al.
4,640,663 A 2/1987 Niinomi et al.
(Continued)

FOREIGN PATENT DOCUMENTS

CN 2910169 Y 6/2007
CN 101049248 A 10/2007
(Continued)

OTHER PUBLICATIONS

Extended European Search Report for Application No. 15855456.8, dated Sep. 25, 2018, 10 pages.
(Continued)

*Primary Examiner* — Ronnie M Mancho
(74) *Attorney, Agent, or Firm* — Artegis Law Group, LLP

(57) ABSTRACT

A system and method for integrated table motion includes a device. The device includes an articulated arm having joints and a distal portion distal to the joints and a control unit. To support integrated motion with a separate table, the control unit is configured to receive a table movement request from the table, determine whether allowing the table movement request would result in a first joint of the joints being at a range of motion limit, allow the table to perform the table movement request based on determining that allowing the table to perform the table movement request would not result in the first joint being at the range of motion limit, track movement of the table due to performing the table movement request, and maintain, using the joints and based
(Continued)

on the tracked movement, a position and/or an orientation of the distal portion relative to the table.

20 Claims, 14 Drawing Sheets

Related U.S. Application Data

(60) Provisional application No. 62/134,207, filed on Mar. 17, 2015, provisional application No. 62/069,245, filed on Oct. 27, 2014.

(51) Int. Cl.
*A61G 13/02* (2006.01)
*A61B 34/00* (2016.01)

(58) Field of Classification Search
USPC ........................................................ 700/254
See application file for complete search history.

(56) References Cited

U.S. PATENT DOCUMENTS

| | | | |
|---|---|---|---|
| 4,693,665 A | 9/1987 | Friederichs et al. | |
| 4,894,855 A | 1/1990 | Kresse | |
| 4,928,047 A | 5/1990 | Arai et al. | |
| 4,945,914 A | 8/1990 | Allen | |
| 5,144,213 A | 9/1992 | Sasaki et al. | |
| 5,222,499 A | 6/1993 | Allen et al. | |
| 5,397,323 A | 3/1995 | Taylor et al. | |
| 5,784,542 A | 7/1998 | Ohm et al. | |
| 5,790,307 A | 8/1998 | Mick et al. | |
| 5,994,864 A | 11/1999 | Inoue et al. | |
| 6,120,433 A | 9/2000 | Mizuno et al. | |
| 6,246,200 B1 | 6/2001 | Blumenkranz et al. | |
| 6,471,165 B2 | 10/2002 | Twisselmann | |
| 6,471,167 B1 | 10/2002 | Myers et al. | |
| 6,560,492 B2 | 5/2003 | Borders | |
| 7,089,612 B2 | 8/2006 | Rocher et al. | |
| 7,155,315 B2 | 12/2006 | Niemeyer et al. | |
| 7,189,246 B2 | 3/2007 | Otsuka et al. | |
| 7,720,322 B2 | 5/2010 | Prisco et al. | |
| 7,741,802 B2 | 6/2010 | Prisco et al. | |
| 7,763,015 B2 | 7/2010 | Cooper et al. | |
| 7,837,674 B2 | 11/2010 | Cooper | |
| 7,852,030 B2 | 12/2010 | Kamiya | |
| 8,004,229 B2 * | 8/2011 | Nowlin | A61B 34/35 318/568.21 |
| 8,069,714 B2 | 12/2011 | Ortmaier et al. | |
| 8,226,072 B2 | 7/2012 | Murayama | |
| 8,271,130 B2 | 9/2012 | Hourtash et al. | |
| 8,400,094 B2 | 3/2013 | Schena | |
| 8,464,720 B1 | 6/2013 | Pigazzi et al. | |
| 8,541,970 B2 | 9/2013 | Nowlin et al. | |
| 8,620,473 B2 | 12/2013 | Diolaiti et al. | |
| 8,624,537 B2 | 1/2014 | Nowlin et al. | |
| 8,641,621 B2 | 2/2014 | Razzaque et al. | |
| 8,749,189 B2 | 6/2014 | Nowlin et al. | |
| 8,749,190 B2 | 6/2014 | Nowlin et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 8,852,208 B2 | 10/2014 | Gomez et al. | |
| 8,918,211 B2 * | 12/2014 | Diolaiti | A61B 34/77 700/257 |
| 9,060,678 B2 | 6/2015 | Larkin et al. | |
| 9,078,686 B2 | 7/2015 | Schena | |
| 9,084,623 B2 | 7/2015 | Gomez et al. | |
| 9,102,058 B2 | 8/2015 | Hofmann et al. | |
| 9,107,683 B2 | 8/2015 | Hourtash et al. | |
| 9,138,129 B2 | 9/2015 | Diolaiti | |
| 9,295,524 B2 | 3/2016 | Schena et al. | |
| 9,296,104 B2 | 3/2016 | Swarup et al. | |
| 9,333,042 B2 | 5/2016 | Diolaiti et al. | |
| 9,334,911 B2 | 5/2016 | Kameta et al. | |
| 9,345,544 B2 | 5/2016 | Hourtash et al. | |
| 9,375,284 B2 | 6/2016 | Hourtash | |
| 9,387,593 B2 | 7/2016 | Bonin et al. | |
| 9,415,510 B2 | 8/2016 | Hourtash et al. | |
| 9,468,501 B2 | 10/2016 | Hourtash et al. | |
| 9,469,034 B2 | 10/2016 | Diolaiti et al. | |
| 9,492,235 B2 | 11/2016 | Hourtash et al. | |
| 9,492,927 B2 | 11/2016 | Diolaiti et al. | |
| 9,918,681 B2 | 3/2018 | Wallace et al. | |
| 10,064,689 B2 | 9/2018 | Swarup et al. | |
| 10,226,306 B2 | 3/2019 | Itkowitz et al. | |
| 10,272,569 B2 | 4/2019 | Swarup et al. | |
| 10,405,944 B2 | 9/2019 | Swarup et al. | |
| 10,555,777 B2 | 2/2020 | Griffiths et al. | |
| 10,617,479 B2 | 4/2020 | Itkowitz et al. | |
| 10,624,807 B2 | 4/2020 | Itkowitz et al. | |
| 2002/0082612 A1 | 6/2002 | Moll et al. | |
| 2002/0161446 A1 | 10/2002 | Bryan et al. | |
| 2003/0192758 A1 | 10/2003 | Murata et al. | |
| 2006/0025668 A1 | 2/2006 | Peterson et al. | |
| 2007/0096670 A1 | 5/2007 | Hashimoto et al. | |
| 2007/0185376 A1 | 8/2007 | Wilson et al. | |
| 2007/0270685 A1 | 11/2007 | Kang et al. | |
| 2008/0004633 A1 | 1/2008 | Arata et al. | |
| 2008/0046122 A1 | 2/2008 | Manzo et al. | |
| 2008/0064921 A1 | 3/2008 | Larkin et al. | |
| 2008/0125649 A1 * | 5/2008 | Meyer | A61B 6/4441 600/426 |
| 2008/0312529 A1 * | 12/2008 | Amiot | A61B 90/36 600/426 |
| 2009/0088774 A1 | 4/2009 | Swarup et al. | |
| 2009/0326324 A1 | 12/2009 | Munoz et al. | |
| 2010/0042097 A1 | 2/2010 | Newton et al. | |
| 2010/0138183 A1 * | 6/2010 | Jensen | A61G 13/10 702/150 |
| 2010/0168762 A1 | 7/2010 | Osawa et al. | |
| 2010/0204713 A1 | 8/2010 | Ruiz et al. | |
| 2010/0228249 A1 | 9/2010 | Mohr et al. | |
| 2010/0228264 A1 | 9/2010 | Robinson et al. | |
| 2010/0292843 A1 * | 11/2010 | Kariyazaki | B25J 9/1676 700/264 |
| 2011/0015521 A1 | 1/2011 | Faul | |
| 2011/0071508 A1 | 3/2011 | Duval et al. | |
| 2012/0029694 A1 * | 2/2012 | Muller | A61B 6/0407 700/248 |
| 2012/0101508 A1 * | 4/2012 | Wook Choi | A61B 34/30 606/130 |
| 2013/0072822 A1 | 3/2013 | Auchinleck et al. | |
| 2013/0085510 A1 | 4/2013 | Stefanchik et al. | |
| 2013/0096701 A1 | 4/2013 | Suorajaervi et al. | |
| 2013/0110129 A1 | 5/2013 | Reid et al. | |
| 2013/0123799 A1 | 5/2013 | Smith et al. | |
| 2013/0327902 A1 | 12/2013 | Frick et al. | |
| 2014/0005654 A1 | 1/2014 | Batross et al. | |
| 2014/0039517 A1 | 2/2014 | Bowling et al. | |
| 2014/0052153 A1 | 2/2014 | Griffiths et al. | |
| 2014/0052154 A1 | 2/2014 | Griffiths et al. | |
| 2014/0055489 A1 * | 2/2014 | Itkowitz | B25J 9/1666 345/633 |
| 2014/0222207 A1 | 8/2014 | Bowling et al. | |
| 2014/0276887 A1 * | 9/2014 | Stein | A61B 5/4851 606/102 |
| 2014/0305995 A1 * | 10/2014 | Shelton, IV | A61B 17/068 227/180.1 |
| 2014/0316430 A1 | 10/2014 | Hourtash et al. | |
| 2014/0358161 A1 * | 12/2014 | Hourtash | A61B 34/37 606/130 |
| 2015/0032126 A1 | 1/2015 | Nowlin et al. | |
| 2015/0051733 A1 | 2/2015 | Nowlin et al. | |
| 2015/0150639 A1 | 6/2015 | Diolaiti et al. | |
| 2015/0224845 A1 | 8/2015 | Anderson et al. | |
| 2016/0081754 A1 | 3/2016 | Kostrzewski et al. | |
| 2017/0079722 A1 | 3/2017 | O'Grady et al. | |
| 2017/0079730 A1 | 3/2017 | Azizian et al. | |
| 2017/0079731 A1 | 3/2017 | Griffiths et al. | |
| 2017/0086932 A1 | 3/2017 | Auld et al. | |
| 2017/0112580 A1 | 4/2017 | Griffiths et al. | |

(56) References Cited

U.S. PATENT DOCUMENTS

| | | |
|---|---|---|
| 2017/0312047 A1 | 11/2017 | Swarup et al. |
| 2017/0333141 A1 | 11/2017 | Itkowitz et al. |
| 2017/0333142 A1 | 11/2017 | Itkowitz et al. |
| 2017/0333145 A1 | 11/2017 | Griffiths et al. |
| 2017/0333275 A1 | 11/2017 | Itkowitz et al. |
| 2017/0334067 A1 | 11/2017 | Swarup et al. |
| 2018/0289427 A1 | 10/2018 | Griffiths et al. |
| 2018/0338808 A1 | 11/2018 | Swarup et al. |
| 2019/0176327 A1 | 6/2019 | Swarup et al. |
| 2019/0328484 A1 | 10/2019 | Swarup et al. |
| 2020/0129244 A1 | 4/2020 | Griffiths et al. |

FOREIGN PATENT DOCUMENTS

| | | |
|---|---|---|
| CN | 101217913 A | 7/2008 |
| CN | 201082167 Y | 7/2008 |
| CN | 101332137 A | 12/2008 |
| CN | 101449292 A | 6/2009 |
| CN | 101466342 A | 6/2009 |
| CN | 101472546 A | 7/2009 |
| CN | 101959656 A | 1/2011 |
| CN | 102046360 A | 5/2011 |
| CN | 101443163 B | 8/2011 |
| CN | 102429726 A | 5/2012 |
| CN | 101234033 B | 6/2012 |
| CN | 103221015 A | 7/2013 |
| CN | 103720514 A | 4/2014 |
| CN | 104002296 B | 5/2016 |
| EP | 1915963 A1 | 4/2008 |
| EP | 2047805 A1 | 4/2009 |
| EP | 2332477 A2 | 6/2011 |
| EP | 2332479 A2 | 6/2011 |
| EP | 2332482 A2 | 6/2011 |
| JP | H05138583 A | 6/1993 |
| JP | H06278063 A | 10/1994 |
| JP | H0884735 A | 4/1996 |
| JP | H09254079 A | 9/1997 |
| JP | H09300264 A | 11/1997 |
| JP | 2000107200 A | 4/2000 |
| JP | 2003299674 A | 10/2003 |
| JP | 2004216022 A | 8/2004 |
| JP | 2004358239 A | 12/2004 |
| JP | 2004538037 A | 12/2004 |
| JP | 2008259607 A | 10/2008 |
| JP | 2010194101 A | 9/2010 |
| JP | 2011212837 A | 10/2011 |
| JP | 2012005557 A | 1/2012 |
| JP | 2012239709 A | 12/2012 |
| JP | 2013252427 A | 12/2013 |
| JP | 2015502768 A | 1/2015 |
| WO | WO-9403113 A1 | 2/1994 |
| WO | WO-2006039092 A2 | 4/2006 |
| WO | WO-2006069288 A2 | 6/2006 |
| WO | WO-2006124390 A2 | 11/2006 |
| WO | WO-2007136768 A2 | 11/2007 |
| WO | WO-2007136770 A2 | 11/2007 |
| WO | WO-2008002830 A2 | 1/2008 |
| WO | WO-2011109041 A1 | 9/2011 |
| WO | WO-2011143016 A1 | 11/2011 |
| WO | WO-2013048957 A1 | 4/2013 |
| WO | WO-2013181503 A1 | 12/2013 |
| WO | WO-2013181507 A1 | 12/2013 |
| WO | WO-2013181516 A1 | 12/2013 |
| WO | WO-2014028703 A1 | 2/2014 |
| WO | WO-2014146095 A1 | 9/2014 |
| WO | WO-2014146107 A1 | 9/2014 |
| WO | WO-2014146113 A1 | 9/2014 |
| WO | WO-2014146119 A1 | 9/2014 |
| WO | WO-2014146120 A1 | 9/2014 |
| WO | WO-2015142798 A1 | 9/2015 |
| WO | WO-2015142930 A1 | 9/2015 |
| WO | WO-2015142943 A1 | 9/2015 |
| WO | WO-2015142947 A1 | 9/2015 |
| WO | WO-2016069648 A1 | 5/2016 |
| WO | WO-2016069655 A1 | 5/2016 |
| WO | WO-2016069659 A1 | 5/2016 |
| WO | WO-2016069660 A1 | 5/2016 |
| WO | WO-2016069661 A1 | 5/2016 |
| WO | WO-2016069663 A1 | 5/2016 |

OTHER PUBLICATIONS

Extended European Search Report for Application No. EP15854136.7, dated Jun. 7, 2018, 11 pages.
Extended European Search Report for Application No. EP15854253, dated May 11, 2018, 11 pages.
Extended European Search Report for Application No. EP15854260.5, dated Jun. 7, 2018, 8 pages.
Extended European Search Report for Application No. EP15855051.7, dated May 3, 2018, 10 pages.
Extended European Search Report for Application No. EP15855097, dated Apr. 25, 2018, 11 pages.
Extended European Search Report for Application No. EP15855351.1, dated Apr. 30, 2018, 9 pages.
Hesse S., et al., "Lexikon Der Elektrischen Antriebstechnik," Festo Didactic GmbH & Co. KG, Jan. 1, 2004, pp. 1-198, XP055260002 [retrieved on Mar. 21, 2016], Retrieved from the Internet:< url:<a href="http://www.boss.festo-cpx.com/pdf/539265_webprint.pdf">http://www.boss.festo-cpx.com/pdf/539265_webprint.pdf</url:<a>.
International Search Report and Written Opinion for Application No. PCT/US2015/057656, dated Feb. 1, 2016, 11 pages.
International Search Report and Written Opinion for Application No. PCT/US2015/057658, dated Feb. 1, 2016, 12 pages.
International Search Report and Written Opinion for Application No. PCT/US2015/057664, dated Feb. 1, 2016, 8 pages.
International Search Report and Written Opinion for Application No. PCT/US2015/057669, dated Feb. 1, 2016, 9 pages.
International Search Report and Written Opinion for Application No. PCT/US2015/057670, dated Feb. 1, 2016, 8 pages.
International Search Report and Written Opinion for Application No. PCT/US2015/057671, dated Feb. 1, 2016, 6 pages.
International Search Report and Written Opinion for Application No. PCT/US2015/057673, dated Feb. 1, 2016, 10 pages.
Partial Supplementary European Search Report for Application No. EP15855456.8, dated May 23, 2018, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP20182993.4, dated Oct. 2, 2020, 13 pages.
Co-pending U.S. Appl. No. 61/954,120, filed Mar. 17, 2014.

* cited by examiner

SYSTEM AND METHOD FOR INTEGRATED TABLE MOTION

RELATED APPLICATIONS

This application is a continuation of U.S. patent application Ser. No. 15/522,169 (filed on Apr. 26, 2017), which is a U.S. National Stage patent application of International Patent Application No. PCT/US2015/057656 (filed on Oct. 27 2015), the benefit of which is claimed, and claims priority to U.S. Provisional Patent Application No. 62/069,245 entitled "System and Method for Integrated Operating Table," which was filed Oct. 27, 2014, and U.S. Provisional Patent Application No. 62/134,207 entitled "System and Method for Integrated Surgical Table," which was filed Mar. 17, 2015, each of which are hereby incorporated by reference in their entirety.

TECHNICAL FIELD

The present disclosure relates generally to operation of devices with articulated arms and more particularly to operation of the devices with the articulated arms with a separate table.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices. As more and more autonomous and semiautonomous devices are placed in use it opens opportunities where two or more of the devices cooperate to achieve a common goal.

It is often desirable for the surgeon or operating room staff to move a patient on an operating or surgical table relative to the manipulator arms of a computer-assisted device being used as a surgical manipulator assembly in order to improve or optimize access to, or visualization of, the patient's internal anatomy. For example, a surgeon may wish to perform a gravity-assisted retraction of an organ during a surgical procedure. Because the patient's organs will move as the surgical table is tilted, for safety the surgical instruments are removed from the patient prior to moving the surgical table. Then, in many conventional teleoperated surgical systems, to perform such a retraction, the manipulator arms must be undocked from the cannulas and instruments inserted into the patient through body openings, such as incision sites and/or body orifices, so that the body openings can safely move, the surgical table must then be moved into a new position estimated to be suitable for retraction of the targeted organ, and then the manipulators re-docked with the patient. This method can be time consuming and cumbersome. Furthermore, this process may involve several iterations, because an endoscope is generally also removed from the patient before the surgical table is moved to improve safety, such that visualization of the surgical workspace is lost and the new position is typically an educated guess, which may or may not be accurate or sufficient to properly perform the retraction. To avoid repeated iterations, physicians often "overcorrect" and select positions and orientations that are steeper than necessary to ensure that the desired gravity-assisted retraction occurs. This overcorrection may lead to patient safety problems, because certain orientations, such as a head down orientation of the patient, may be poorly tolerated by a patient, and particularly by larger patients who often have difficulty breathing in such an orientation. In addition, because the instruments are removed from the patient and the manipulator arms are removed from the cannulas, the instruments cannot be used by a physician to assist with the retraction, such as may be done in a traditional laparoscopic procedure.

Accordingly, it would be advantageous to have systems and methods that allow for movement in a surgical table without first having to remove a computer-assisted device with a manipulator and instrument assembly from the patient.

SUMMARY

Advantageously, systems and methods in accordance with the present invention allow the surgical table (with the patient) to be moved relative to the surgical instrument manipulator arms without first having to remove the manipulator-controlled surgical instruments from the patient and undock the manipulators from the cannulas that stay inserted in the patient. In one aspect, bi-directional communication is first established between the computer-assisted medical device with manipulator arms and the surgical table. After this communication is established, control of motion in the surgical table motion is then subject to control by the computer-assisted device such that no physical surgical table motion is allowed without first receiving permission and/or approval from computer-assisted device.

In one aspect, when the patient is moved, one of the operating room staff (e.g., the anesthesiologist) will initiate the move (for example, by pressing a button on a surgical table command unit). The desired command for the desired movement (e.g., adjust a Trendelenburg orientation to raise or lower the patient's head, tilt patient left or tilt patient right, and/or raise or lower a table surface) is relayed to the computer-assisted device via a communications link. The controller for the computer-assisted device then determines whether the desired move is allowable based on current conditions or states of the integrated system (e.g., physical, electrical, and/or software conditions). The surgical table move request is then either approved or denied via a return message to the surgical table. When the surgical table move request is approved, the surgical table is allowed to move in the commanded direction in an incremental manner (e.g., increments of distance, angle, or time) as described below. In addition, in certain aspects table motion velocity is controlled to be fast enough to allow a surgeon viewing tissue motion via an imaging device, such as an endoscope, to see effective tissue movement due to gravity, and slow enough so that there is no appreciable danger to the patient or personnel near the surgical table or computer-assisted device. In one aspect it is desirable for movement of the surgical table during the motion to be controlled to less than 3 degrees per second (e.g., about 1.5 degrees per second). This rate provides suitable movement to reposition the surgical table in an efficient manner, but is slow enough so that intermittent permissions from the control system to prevent problematic computer-assisted device conditions and/or injury to the patient from developing.

In another aspect, when the computer-assisted device detects a relevant change in a state of the manipulator arms during surgical table motion (for example, an approaching range of motion limit in an articulated joint), the computer-assisted device halts the surgical table motion to prevent injury to the patient or staff and/or damage to equipment. This cycle of requesting a move, approving or denying the request, then moving is then repeated in rapid succession, for example every 10 ms, for each individual table control button press and/or stream of commands (e.g., button held down condition). As long as the computer-assisted device state is considered "safe" or acceptable, the surgical table move requests are approved by the computer-assisted device, and the surgical table is free to move in any direction commanded by the operator.

In one aspect, when a surgical table move request is denied, or in the event of the computer-assisted device interrupting a currently executing surgical table move, such as due to a range of motion limit in the computer-assisted device, surgical table motion is limited to provide added safety in the use of the system. In some examples, kinematic mappings between the surgical table and the computer-assisted device are used to determine surgical table motions that result in remote center of motion and/or joint velocities away from the range of motion limits and/or unsafe conditions. In some examples, the surgical table motions are limited to motions that are in the opposite direction of the surgical table motion that created the deny/stop condition will be approved. In some examples, no further surgical table motion is allowed when surgical table motion results in two or more articulated arms nearing and/or reaching opposing range of motion limits.

In certain aspects, the surgical table moves around a single point in space (a virtual center of motion point), often called an isocenter. In one implementation, for example, this isocenter is located approximately centered over the articulated structure of the surgical table, and slightly above (e.g., approximately 35 cm), the top of the surgical table to account for typical patient size, insufflation, surgical table padding, and/or the like. Thus, as the surgical table moves in its Trendelenburg adjustments, the table surface travels through a slight "dishing" arc. The surgical table tilt degree of freedom may similarly move with reference to the isocenter point, or it may move with reference to another point in space, such as the top of the column supporting the table top. The surgical table may also include a yaw degree of freedom, either defined with reference to the isocenter or to another point. The isocenter is often located to be inside the patient approximately at a height of a typical surgical site and/or or a body opening, such as an incision site or body orifice, with reference to the table top. In some implementations the isocenter is fixed with reference to the table mechanism, and in other implementations the isocenter may be defined (e.g., height and/or location) to accommodate various patient sizes and surgical site locations.

In certain aspects, the computer-assisted device may provide the XYZ Cartesian coordinates of the isocenter to the surgical table, followed by specific roll-pitch-yaw angular motion commands to effect patient movement. Such motions might provide enhanced clinical capability to the surgeon because in some situations they minimize the total motion of the relevant body openings in the patient's body wall, which minimizes physical trauma at the body openings through which instruments are inserted. In one aspect, such motion commands might be generated by the surgeon's motion of surgical controllers for the surgical instruments or instruments used to perform the procedure. The XYZ-Roll-Pitch-Yaw coordinates and commands are sent to the surgical table via the same communications link described in the first mode of operation. It should be noted that in order for such isocenter motion to take place, the position and/or orientation of the surgical table relative to the computer-assisted device should be known by the computer-assisted device. This relationship may be input by a user or determined by the computer-assisted device by any suitable means. In one aspect, this relationship may be determined by a registration, such as described in U.S. Provisional Patent Application No. 61/954,538 entitled "Methods and Devices for Tele-surgical Table Registration," which was filed Mar. 17, 2014 or it may be determined or estimated by a location means, such as described in U.S. Provisional Patent Application No. 61/954,559 entitled "Methods and Devices for Table Pose Tracking using Fiducial Markers," which was filed Mar. 17, 2014, each of which is incorporated by reference herein in its entirety for all purposes.

In the computer-assisted device, a multiple degree of freedom manipulator holds the surgical instruments, and in turn a multi-link set up arm holds the manipulator with reference to a mechanical ground. The manipulator is teleoperated, and the setup arm may be moved by hand. Mechanical brakes may be used to hold the links in place (hardware locking of the joints), and in addition motorized joints may be used to hold unbraked links in place (software locking of the joints). In some aspects, some or all of the mechanical brakes may be released so that either the entire setup/manipulator arm can "float" (appear effectively weightless), or a portion of the entire setup/manipulator arm can float. In some situations, this release of brakes (hardware and/or software) is referred to as clutching. By clutching the brakes associated with a joint, a link may be allowed to move. When an articulated arm is clutched, it may be mechanically balanced and controlled to remain stationary in space until moved. In some aspects, the external movement comes from instrument dragging where force against the cannula by the body wall of the patient as the patient is moved (e.g., by moving the surgical table) results in changes in the positions and/or orientations of the clutched arm joints.

In certain conventional teleoperated surgical manipulator systems having the same or similar kinematics as the embodiments described herein, it is not recommended to move the patient while the instruments are inserted into the patient by the cannulas. In such systems, the current set up arm joints may not have low enough friction to allow instrument dragging by the patient's body wall and, more importantly, there is no current way for the surgical table motion to be stopped in the event that one of the clutched joints reaches a range of motion limit. Continuing to move the surgical table with the patient under these conditions may result in harm to the patient, particularly at the body opening through which the instrument is inserted. Therefore, an "interlock" aspect allows the surgical table to be moved but safely stopped in the event that the computer-assisted device determines or detects an unsafe (or impending unsafe) condition.

In one aspect, the withdrawal feature (i.e., "go back the way you came") allows the surgical table to be moved back along its immediately preceding motion path and may further allow or enable other direction approaches or patient motions. In a safety aspect, all computer-assisted device and surgical table motion is typically prohibited when the computer-assisted device detects an unsafe condition, and motion is not permitted until the unsafe condition is resolved. Without this withdrawal feature, when the surgical table is stopped (via automatic command from the computer-assisted device), the surgical table may not be able to move again because the computer-assisted device would be in an unsafe condition (e.g., the condition that generated the "stop" command still being present). Thus, by using previously known positions/movements, the withdrawal feature ensures a safe surgical table move because it is permitted to go back along the path that resulted in the unsafe condition. While motion along certain other axes may possibly be "safe," such axes are not known to be safe. In certain embodiments, the isocenter motion capability is an advancement beyond the interlocking nature of the system.

By using the methods and systems described herein, a surgeon is able to move the patient in a safe manner because the computer-assisted device may command the surgical table to stop before large forces are applied to the patient via the cannulas. The surgical table motion may then be reversed "back the way it came" to keep from remaining in an unsafe or potentially unsafe pose until the detected condition is resolved.

Consistent with some embodiments, a computer-assisted medical device includes an articulated arm having one or more first joints and one or more second joints and a control unit coupled to the first joints and the second joints. The articulated arm is configured to have at least a cannula, an endoscope, or an instrument mounted distal to the one or more first joints and the one or more second joints. The cannula, the endoscope, or the instrument is configured to be inserted into a patient at a body opening. To support integrated motion with a surgical table coupled to the device via a communications connection, the control unit is configured to unlock the one or more first joints, receive a surgical table movement request from the surgical table, determine whether the surgical table movement request should be granted, allow the surgical table to perform the surgical table movement request based on the determining, use the one or more first joints to allow the articulated arm to track movement of the body opening based on forces applied by a body wall of the patient at the body opening due to the performed surgical table movement, and compensate for changes in a pose of the cannula, the endoscope, or the instrument due to the tracked movement by performing compensating motions in the one or more second joints.

Consistent with some embodiments, a method of compensating for integrated motion of a surgical table and a computer-assisted medical device includes unlocking one or more joints of an articulated arm of the computer-assisted medical device. The articulated arm has at least a cannula, an endoscope, or an instrumented mounted thereto. The cannula, the endoscope, or the instrument is configured to be inserted into a patient at a body opening. The method further includes receiving a surgical table movement request from a surgical table, determining whether the surgical table movement request should be granted, allowing the surgical table to perform the surgical table movement request based on the determining, using the one or more first joints to allow the articulated arm to track movement of the body opening based on forces applied by a body wall of the patient at the body opening due to the performed surgical table movement, and compensating for changes in a pose of the cannula, the endoscope, or the instrument due to the tracked movement by performing compensating motions in one or more second joints of the articulated arm.

Consistent with some embodiments, a non-transitory machine-readable medium including a plurality of machine-readable instructions which when executed by one or more processors associated with a computer-assisted medical device are adapted to cause the one or more processors to perform a method. The method includes unlocking one or more joints of an articulated arm of the computer-assisted medical device. The articulated arm has at least a cannula, an endoscope, or an instrumented mounted thereto. The cannula, the endoscope, or the instrument is configured to be inserted into a patient at a body opening. The method further includes receiving a surgical table movement request from a surgical table, determining whether the surgical table movement request should be granted, allowing the surgical table to perform the surgical table movement request based on the determining, using the one or more first joints to allow the articulated arm to track movement of the body opening based on forces applied by a body wall of the patient at the body opening site due to the performed surgical table movement, and compensating for changes in a pose of the cannula, the endoscope, or the instrument due to the tracked movement by performing compensating motions in one or more second joints of the articulated arm.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. The term "including" means including but not limited to, and each of the one or more individual items included should be considered optional unless otherwise stated. Similarly, the term "may" indicates that an item is optional.

Figure 1:
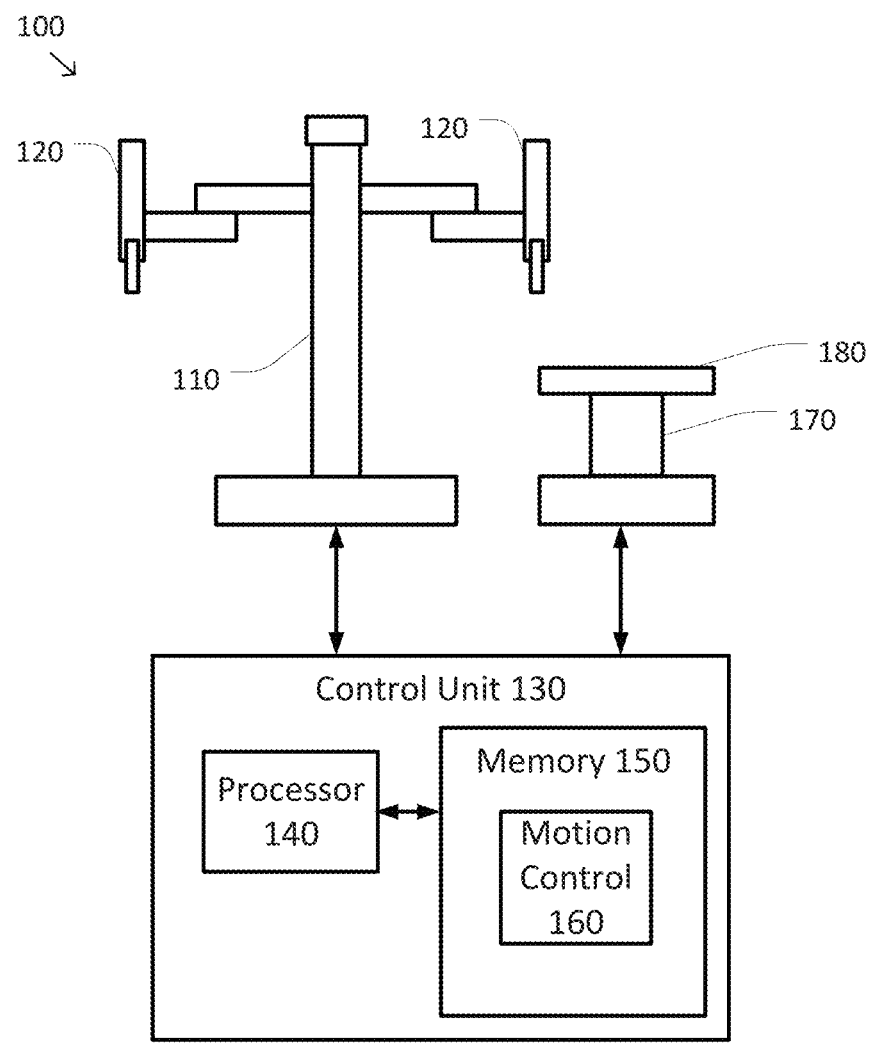
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 supports one or more end effectors. In some examples, device 110 may be consistent with a computer-assisted surgical device. The one or more articulated arms 120 each provides support for one or more instruments, surgical instruments, imaging devices, and/or the like mounted to a distal end of at least one of the articulated arms 120. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may optionally be used with computer-assisted system 100.

Device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 is used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that supports autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, such as a surgical table and/or imaging device, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Computer-assisted system 100 further includes a surgical table 170. Like the one or more articulated arms 120, surgical table 170 supports articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a surgical table command unit for controlling the position and/or orientation of table top 180. In some embodiments, surgical table 170 may correspond to one or more of the surgical tables commercialized by Trumpf Medical Systems GmbH of Germany.

Surgical table 170 is also coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, motion control application 160 may include one or more application programming interfaces (APIs) for receiving position, motion, and/or other sensor information associated with surgical table 170 and/or table top 180. In some examples, motion control application 160 may plan and/or assist in the planning of motion for surgical table 170 and/or table top 180. In some examples, motion control application 160 may contribute to motion plans associated with collision avoidance, adapting to and/or avoid range of motion limits in joints and links, movement of articulated arms, instruments, end effectors, surgical table components, and/or the like to compensate for other motion in the articulated arms, instruments, end effectors, surgical table components, and/or the like, adjust a viewing device such as an endoscope to maintain and/or place an area of interest and/or one or more instruments or end effectors within a field of view of the viewing device. In some examples, motion control application 160 may prevent motion of surgical table 170 and/or table top 180, such as by preventing movement of surgical table 170 and/or table top 180 through use of the surgical table command unit. In some examples, motion control application 160 may help register device 110 with surgical table 170 so that a geometric relationship between device 110 and surgical table 170 is known. In some examples, the geometric relationship may include a translation and/or one or more rotations between coordinate frames maintained for device 110 and surgical table 170.

Figure 2:
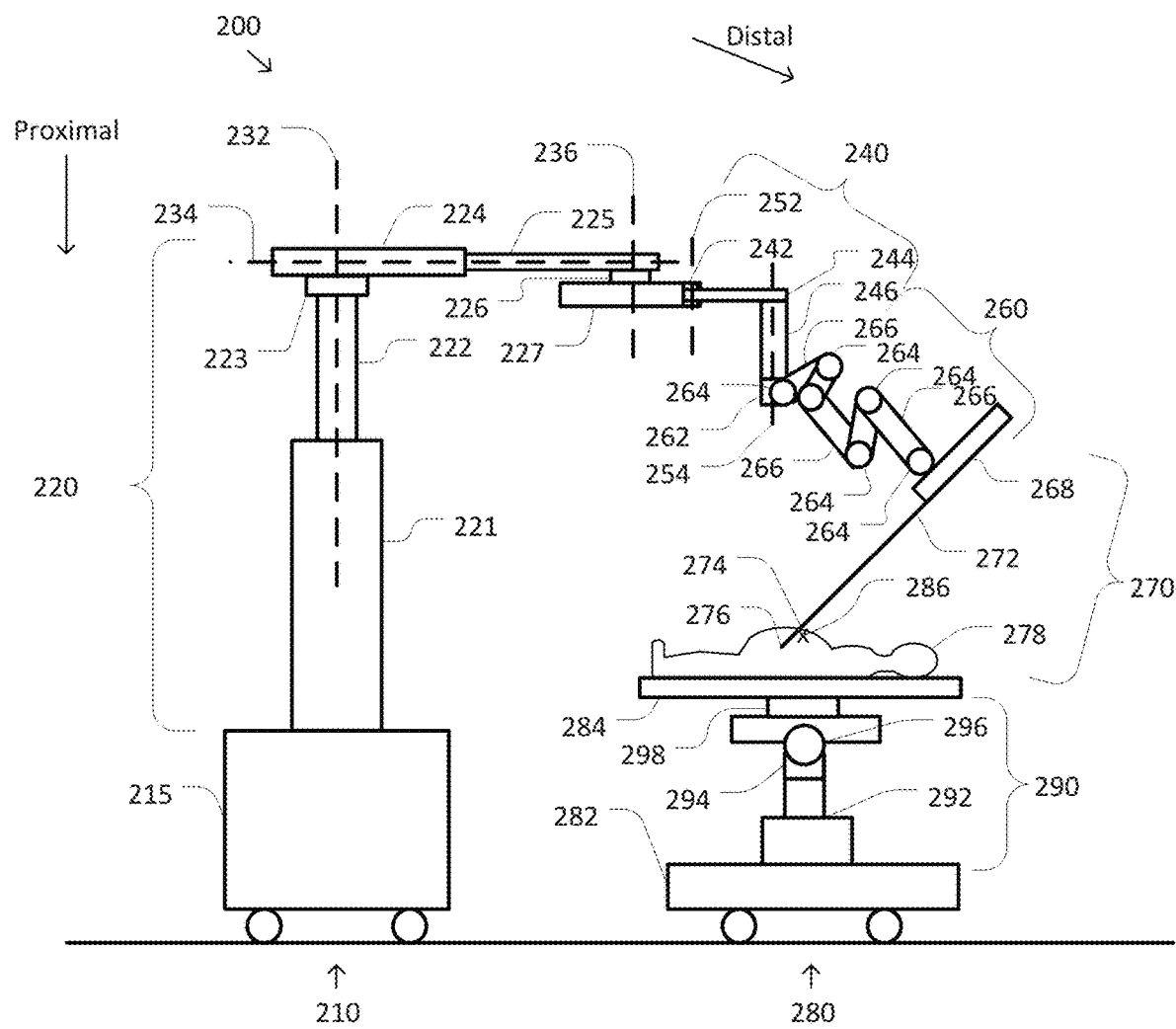
FIG. 2 is a simplified diagram showing a computer-assisted system according to some embodiments.

FIG. 2 is a simplified diagram showing a computer-assisted system 200 according to some embodiments. For example, the computer-assisted system 200 may be consistent with computer-assisted system 100. As shown in FIG. 2, the computer-assisted system 200 includes a computer-assisted device 210 with one or more articulated arms and a surgical table 280. Although not shown in FIG. 2, the computer-assisted device 210 and the surgical table 280 are coupled together using one or more interfaces and one or more control units so that at least kinematic information about the surgical table 280 is known to the motion control application being used to perform motion of the articulated arms of the computer-assisted device 210.

The computer-assisted device 210 includes various links and joints. In the embodiments of FIG. 2, the computer-assisted device is generally divided into three different sets of links and joints. Starting at the proximal end with a mobile cart 215 or patient-side cart 215 is a set-up structure 220. Coupled to a distal end of the set-up structure is a series of links and set-up joints 240 forming an articulated arm. And coupled to a distal end of the set-up joints 240 is a multi-jointed manipulator 260. In some examples, the series of set-up joints 240 and manipulator 260 may correspond to one of the articulated arms 120. And although the computer-assisted device is shown with only one series of set-up joints 240 and a corresponding manipulator 260, one of ordinary skill would understand that the computer-assisted device may include more than one series of set-up joints 240 and corresponding manipulators 260 so that the computer-assisted device is equipped with multiple articulated arms.

As shown, the computer-assisted device 210 is mounted on the mobile cart 215. The mobile cart 215 enables the computer-assisted device 210 to be transported from location to location, such as between operating rooms or within an operating room to better position the computer-assisted device in proximity to the surgical table 280. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an arm mounting platform 227.

The links and joints of the set-up structure 220 include various degrees of freedom for changing the position and orientation (i.e., the pose) of the arm mounting platform 227. For example, the two-part column is used to adjust a height of the arm mounting platform 227 by moving the shoulder joint 223 up and down along an axis 232. The arm mounting platform 227 is additionally rotated about the mobile cart 215, the two-part column, and the axis 232 using the shoulder joint 223. The horizontal position of the arm mounting platform 227 is adjusted along an axis 234 using the two-part boom. And the orientation of the arm mounting platform 227 may also adjusted by rotation about an arm mounting platform orientation axis 236 using the wrist joint 226. Thus, subject to the motion limits of the links and joints in the set-up structure 220, the position of the arm mounting platform 227 may be adjusted vertically above the mobile cart 215 using the two-part column. The positions of the arm mounting platform 227 may also be adjusted radially and angularly about the mobile cart 215 using the two-part boom and the shoulder joint 223, respectively. And the angular orientation of the arm mounting platform 227 may also be changed using the wrist joint 226.

The arm mounting platform 227 is used as a mounting point for one or more articulated arms. The ability to adjust the height, horizontal position, and orientation of the arm mounting platform 227 about the mobile cart 215 provides a flexible set-up structure for positioning and orienting the one or more articulated arms about a work space located near the mobile cart 215 where an operation or procedure is to take place. For example, arm mounting platform 227 may be positioned above a patient so that the various articulated arms and their corresponding manipulators and instruments have sufficient range of motion to perform a surgical procedure on the patient. FIG. 2 shows a single articulated arm coupled to the arm mounting platform 227 using a first set-up joint 242. And although only one articulated arm is shown, one of ordinary skill would understand that multiple articulated arms may be coupled to the arm mounting platform 227 using additional first set-up joints.

The first set-up joint 242 forms the most proximal portion of the set-up joints 240 section of the articulated arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the arm mounting platform 227 about an axis 252 using the first set-up joint 242, adjust a radial or horizontal distance between the first set-up joint 242 and the link 246, adjust a height of a manipulator mount 262 at the distal end of link 246 relative to the arm mounting platform 227 along an axis 254, and rotate the manipulator mount 262 about axis 254. In some examples, the set-up joints 240 may further include additional joints, links, and axes permitting additional degrees of freedom for altering a pose of the manipulator mount 262 relative to the arm mounting platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument 270 is mounted to the instrument carriage 268. Instrument 270 includes a shaft 272, which is aligned along an insertion axis. The shaft 272 is typically aligned so that it passes through a remote center of motion 274 associated with the manipulator 260. Location of the remote center of motion 274 is typically maintained in a fixed translational relationship relative to the manipulator mount 262 so that operation of the joints 264 in the manipulator 260 result in rotations of the shaft 272 about the remote center of motion 274. Depending upon the embodiment, the fixed translational relationship of the remote center of motion 274 relative to the manipulator mount 262 is maintained using physical constraints in the joints 264 and links 266 of the manipulator 260, using software constraints placed on the motions permitted for the joints 264, and/or a combination of both. Representative embodiments of computer-assisted surgical devices using remote centers of motion maintained using physical constraints in joints and links are described in U.S. patent application Ser. No. 13/906,888 entitled "Redundant Axis and Degree of Freedom for Hardware-Constrained Remote Center Robotic Manipulator," which was filed May 13, 2013, and representative embodiments of computer-assisted surgical devices using remote centers of motion maintained by software constraints are described in U.S. Pat. No. 8,004,229 entitled "Software Center and Highly Configurable Robotic Systems for Surgery and Other Uses," which was filed May 19, 2005, the specifications of which are hereby incorporated by reference in their entirety In some examples, the remote center of motion 274 may correspond to a location of a body opening, such as an incision site or body orifice, in a patient 278 where shaft 272 is inserted into the patient 278. Because the remote center of motion 274 corresponds to the body opening, as the instrument 270 is used, the remote center of motion 274 remains stationary relative to the patient 278 to limit stresses on the anatomy of the patient 278 at the remote center of motion 274. In some examples, the shaft 272 may be optionally passed through a cannula (not shown) located at the body opening. In some examples, instruments having a relatively larger shaft or guide tube outer diameter (e.g., 4-5 mm or more) may be passed through the body opening using a cannula and the cannula may optionally be omitted for instruments having a relatively smaller shaft or guide tube outer diameter (e.g., 2-3 mm or less).

At the distal end of the shaft 272 is an end effector 276. The degrees of freedom in the manipulator 260 due to the joints 264 and the links 266 may permit at least control of the roll, pitch, and yaw of the shaft 272 and/or the end effector 276 relative to the manipulator mount 262. In some examples, the degrees of freedom in the manipulator 260 may further include the ability to advance and/or withdraw the shaft 272 using the instrument carriage 268 so that the end effector 276 may be advanced and/or withdrawn along the insertion axis and relative to the remote center of motion 274. In some examples, the manipulator 260 may be consistent with manipulators for use with the da Vinci® Surgical System commercialized by Intuitive Surgical, Inc. of Sunnyvale, Calif. In some examples, the instrument 270 may be an imaging device such as an endoscope, a gripper, a surgical instrument such as a cautery or a scalpel, and/or the like. In some examples, the end effector 276 may include additional degrees of freedom, such as roll, pitch, yaw, grip, and/or the like that allow for additional localized manipulation of portions of the end effector 276 relative to the distal end of the shaft 272.

During a surgery or other medical procedure, the patient 278 is typically located on the surgical table 280. The surgical table 280 includes a table base 282 and a table top 284, with the table base 282 being located in proximity to mobile cart 215 so that the instrument 270 and/or end effector 276 may be manipulated by the computer-assisted device 210 while the shaft 272 of instrument 270 is inserted into the patient 278 at the body opening. The surgical table 280 further includes an articulated structure 290 that includes one or more joints or links between the table base 282 and the table top 284 so that the relative location of the table top 284, and thus the patient 278, relative to the table base 282 is controlled. In some examples, the articulated structure 290 may be configured so that the table top 284 is controlled relative to a virtually-defined table motion isocenter 286 that may be located at a point above the table top 284. In some examples, isocenter 286 may be located within the interior of the patient 278. In some examples, isocenter 286 may be collocated with the body wall of the patient at or near one of the body openings, such as a body opening site corresponding to remote center of motion 274.

As shown in FIG. 2, the articulated structure 290 includes a height adjustment joint 292 so that the table top 284 may be raised and/or lowered relative to the table base 282. The articulated structure 290 further includes joints and links to change both the tilt 294 and Trendelenburg 296 orientation of the table top 284 relative to the isocenter 286. The tilt 294 allows the table top 284 to be tilted side-to-side so that either the right or left side of the patient 278 is rotated upward relative to the other side of the patient 278 (i.e., about a longitudinal or head-to-toe (cranial-caudal) axis of the table top 284). The Trendelenburg 296 allows the table top 284 to be rotated so that either the feet of the patient 278 are raised (Trendelenburg) or the head of the patient 278 is raised (reverse Trendelenburg). In some examples, either the tilt 294 and/or the Trendelenburg 296 rotations may be adjusted to generate rotations about isocenter 286. The articulated structure 290 further includes additional links and joints 298 to slide the table top 284 along the longitudinal (cranial-caudal) axis relative to the table base 282 with generally a left and/or right motion as depicted in FIG. 2.

FIGS. 11A-11G are simplified schematic views that illustrate various computer-assisted device system architectures that incorporate the integrated computer-assisted device and movable surgical table features described herein. The various illustrated system components are in accordance with the principles described herein. In these illustrations, the components are simplified for clarity, and various details such as individual links, joints, manipulators, instruments, end effectors, etc. are not shown, but they should be understood to be incorporated in the various illustrated components.

In these architectures, cannulas associated with one or more surgical instruments or clusters of instruments are not shown, and it should be understood that cannulas and other instrument guide devices optionally may be used for instruments or instrument clusters having a relatively larger shaft or guide tube outer diameter (e.g., 4-5 mm or more) and optionally may be omitted for instruments having a relatively smaller shaft or guide tube outer diameter (e.g., 2-3 mm or less).

Also in these architectures, teleoperated manipulators should be understood to include manipulators that during surgery define a remote center of motion by using hardware constraints (e.g., fixed intersecting instrument pitch, yaw, and roll axes) or software constraints (e.g., software-constrained intersecting instrument pitch, yaw, and roll axes). A hybrid of such instrument axes of rotation may be defined (e.g., hardware-constrained roll axis and software-constrained pitch and yaw axes) are also possible. Further, some manipulators may not define and constrain any surgical instrument axes of rotation during a procedure, and some manipulators may define and constrain only one or two instrument axes of rotation during a procedure.

Figure 11A:
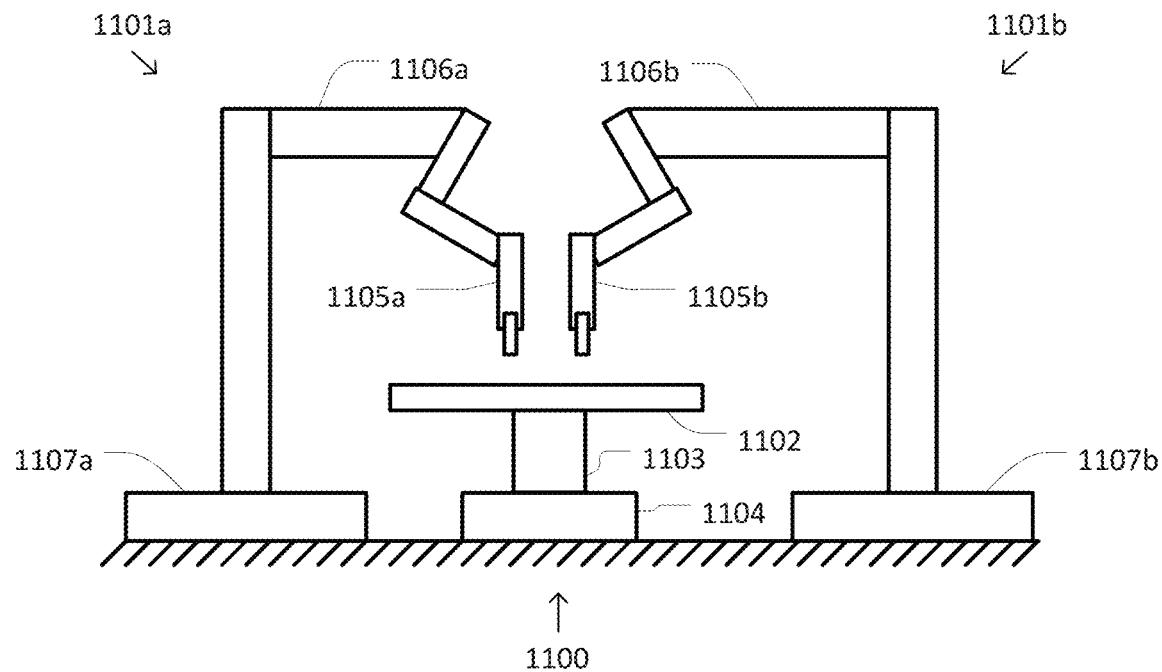
FIGS. 11A-11G are simplified schematic views that illustrate various computer-assisted device system architectures that incorporate the integrated computer-assisted device and movable surgical table features described herein.

FIG. 11A illustrates a movable surgical table 1100 and a single-instrument computer-assisted device 1101a are shown. Surgical table 1100 includes a movable table top 1102 and a table support structure 1103 that extends from a mechanically grounded table base 1104 to support the table top 1102 at a distal end. In some examples, surgical table 1100 may be consistent with surgical table 170 and/or 280. Computer-assisted device 1101a includes a teleoperated manipulator and a single instrument assembly 1105a. Computer-assisted device 1101a also includes a support structure 1106a that is mechanically grounded at a proximal base 1107a and that extends to support manipulator and instrument assembly 1105a at a distal end. Support structure 1106a is configured to allow assembly 1105a to be moved and held in various fixed poses with reference to surgical table 1100. Base 1107a is optionally permanently fixed or movable with reference to surgical table 1100. Surgical table 1100 and computer-assisted device 1101a operate together as described herein.

FIG. 11A further shows an optional second computer-assisted device 1101b, which illustrates that two, three, four, five, or more individual computer-assisted devices may be included, each having a corresponding individual teleoperated manipulator and single-instrument assembly(ies) 1105b supported by a corresponding support structure 1106b. Computer-assisted device 1101b is mechanically grounded, and assemblies 1105b are posed, similarly to computer-assisted device 1101a. Surgical table 1100 and computer-assisted devices 1101a and 1101b together make a multi-instrument surgical system, and they operate together as described herein. In some examples, computer-assisted devices 1101a and/or 1101b may be consistent with computer-assisted devices 110 and/or 210.

Figure 11B:
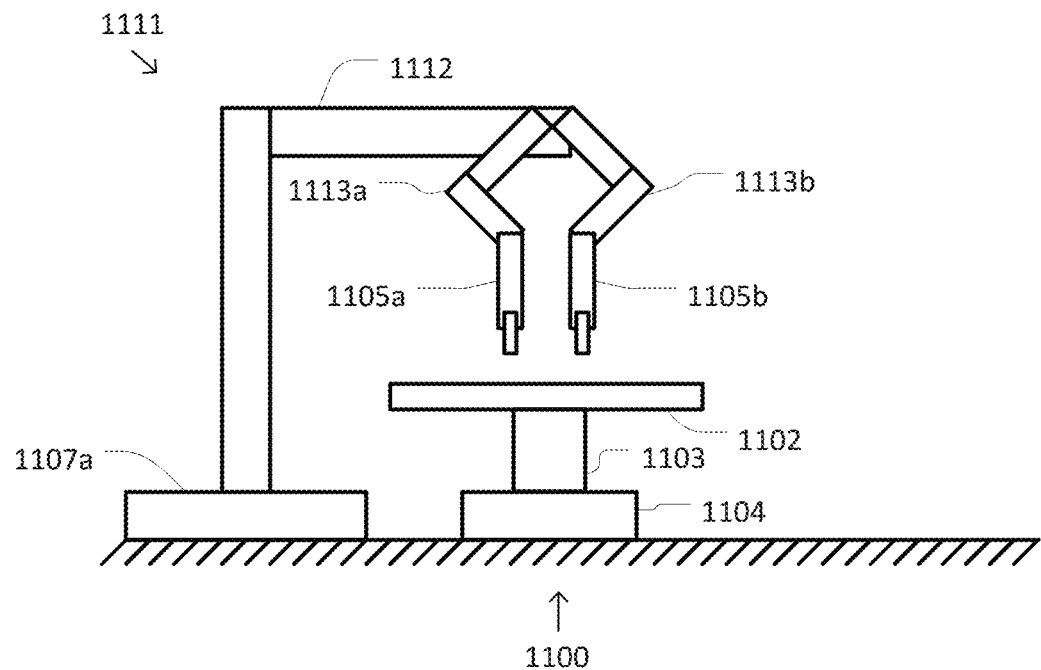

As shown in FIG. 11B, another movable surgical table 1100 and a computer-assisted device 1111 are shown. Computer-assisted device 1111 is a multi-instrument device that includes two, three, four, five, or more individual teleoperated manipulator and single-instrument assemblies as shown by representative manipulator and instrument assemblies 1105a and 1105b. The assemblies 1105a and 1105b of computer-assisted device 1111 are supported by a combined support structure 1112, which allows assemblies 1105a and 1105b to be moved and posed together as a group with reference to surgical table 1100. The assemblies 1105a and 1105b of computer-assisted device 1111 are also each supported by a corresponding individual support structure 1113a and 1113b, respectively, which allows each assembly 1105a and 1105b to be individually moved and posed with reference to surgical table 1100 and to the one or more other assemblies 1105a and 1105b. Examples of such a multi-instrument surgical system architecture are the da Vinci Si® Surgical System and the da Vinci® Xi™ Surgical System, commercialized by Intuitive Surgical, Inc. Surgical table 1100 and a surgical manipulator system comprising an example computer-assisted device 1111 operate together as described herein. In some examples, computer-assisted device 1111 is consistent with computer-assisted devices 110 and/or 210.

Figure 11C:
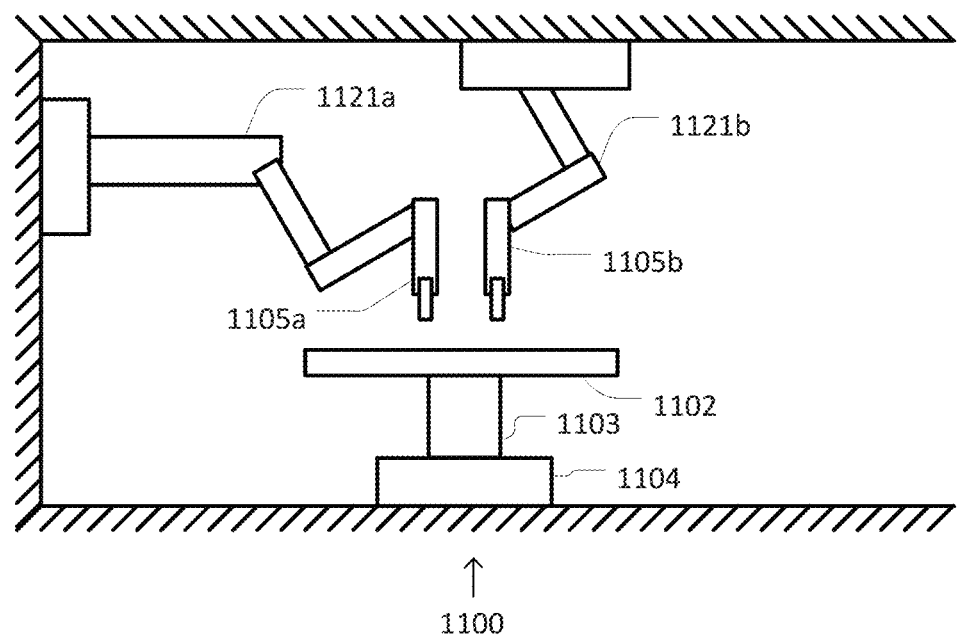

The computer-assisted devices of FIGS. 11A and 11B are each shown mechanically grounded at the floor. But, one or more such computer-assisted devices may optionally be mechanically grounded at a wall or ceiling and be permanently fixed or movable with reference to such a wall or ceiling ground. In some examples, computer-assisted devices may be mounted to the wall or ceiling using a track or grid system that allows the support base of the computer-assisted systems to be moved relative to the surgical table. In some examples, one or more fixed or releasable mounting clamps may be used to mount the respective support bases to the track or grid system. As shown in FIG. 11C, a computer-assisted device 1121a is mechanically grounded at a wall, and a computer-assisted device 1121b is mechanically grounded at a ceiling.

Figure 11D:
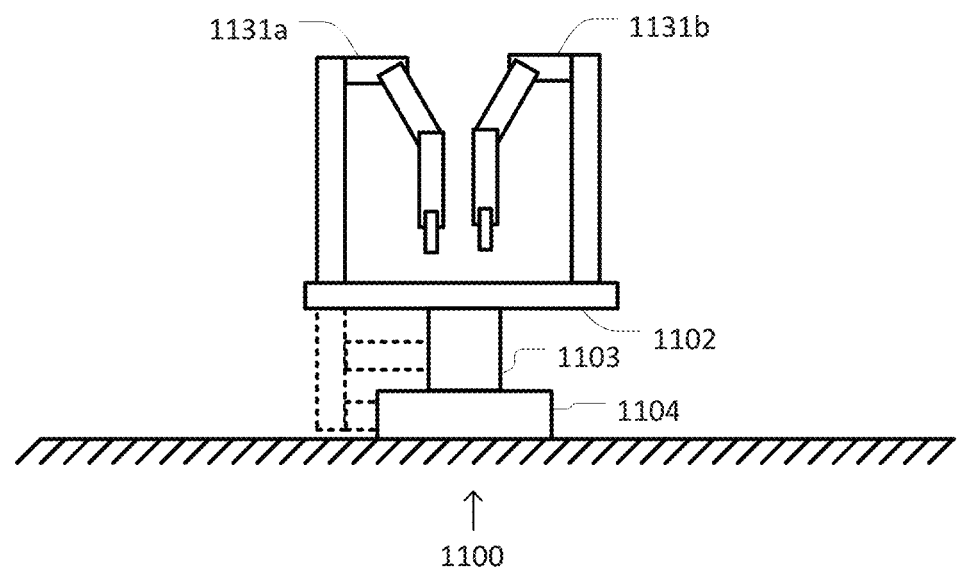

In addition, computer-assisted devices may be indirectly mechanically grounded via the movable surgical table 1100. As shown in FIG. 11D, a computer-assisted device 1131a is coupled to the table top 1102 of surgical table 1100. Computer-assisted device 1131a may optionally be coupled to other portions of surgical table 1100, such as table support structure 1103 or table base 1104, as indicated by the dashed structures shown in FIG. 11D. When table top 1102 moves with reference to table support structure 1103 or table base 1104, the computer-assisted device 1131a likewise moves with reference to table support structure 1103 or table base 1104. When computer-assisted device 1131a is coupled to table support structure 1103 or table base 1104, however, the base of computer-assisted device 1131a remains fixed with reference to ground as table top 1102 moves. As table motion occurs, the body opening where instruments are inserted into the patient may move as well because the patient's body may move and change the body opening locations relative to the table top 1102. Therefore, for embodiments in which computer-assisted device 1131a is coupled to the table top 1102, the table top 1102 functions as a local mechanical ground, and the body openings move with reference to the table top 1102, and so with reference to the computer-assisted device 1131a as well. FIG. 11D also shows that a second computer-assisted device 1131b optionally may be added, configured similarly to computer-assisted device 1131a to create a multi-instrument system. Systems that include one or more computer-assisted device coupled to the surgical table operate as disclosed herein.

In some embodiments, other combinations of computer-assisted devices with the same or hybrid mechanical groundings are possible. For example, a system may include one computer-assisted device mechanically grounded at the floor, and a second computer-assisted device mechanically grounded to the floor via the surgical table. Such hybrid mechanical ground systems operate as disclosed herein.

Figure 11E:
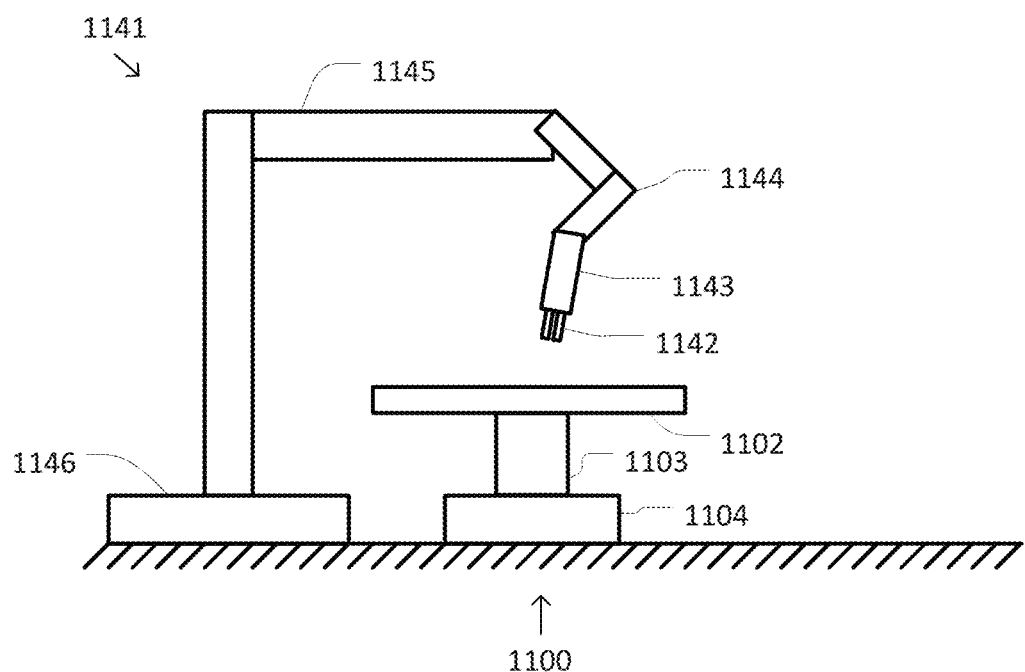

Inventive aspects also include single-body opening systems in which two or more surgical instruments enter the body via a single body opening. Examples of such systems are shown in U.S. Pat. No. 8,852,208 entitled "Surgical System Instrument Mounting," which was filed Aug. 12, 2010, and U.S. Pat. No. 9,060,678 entitled "Minimally Invasive Surgical System," which was filed Jun. 13, 2007, both of which are incorporated by reference. FIG. 11E illustrates a teleoperated multi-instrument computer-assisted device 1141 together with surgical table 1100 as described above. Two or more instruments 1142 are each coupled to a corresponding manipulator 1143 and the cluster of instruments 1142 and instrument manipulators 1143 are moved together by a system manipulator 1144. The system manipulator 1144 is supported by a support assembly 1145 that allows system manipulator 1144 to be moved to and fixed at various poses. Support assembly 1145 is mechanically grounded at a base 1146 consistent with the descriptions above. The two or more instruments 1142 are inserted into the patient at the single body opening. Optionally, the instruments 1142 extend together through a single guide tube, and the guide tube optionally extends through a cannula, as described in the references cited above. Computer-assisted device 1141 and surgical table 1100 operate together as described herein.

Figure 11F:
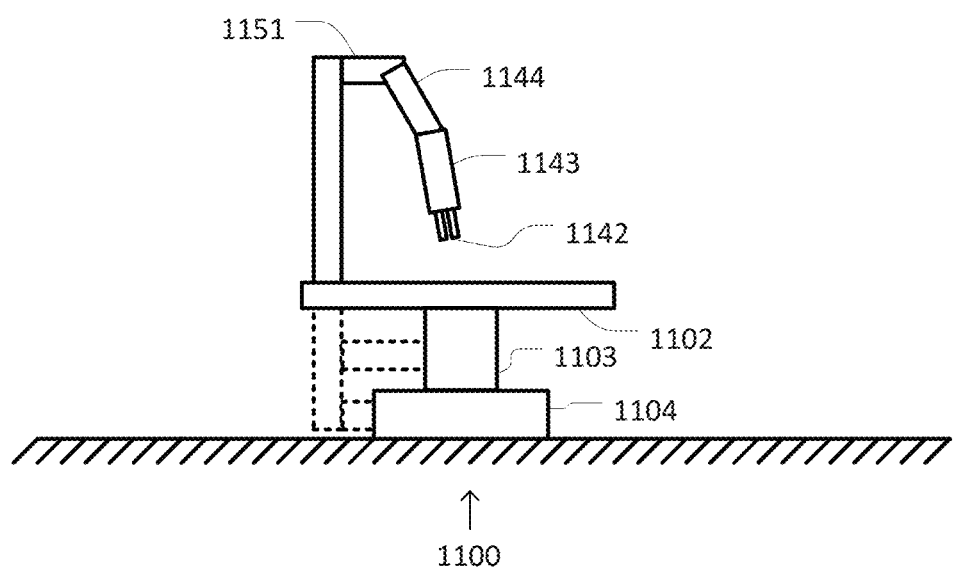

FIG. 11F illustrates another multi-instrument, single-body opening computer-assisted device 1151 mechanically grounded via the surgical table 1100, optionally by being coupled to table top 1102, table support structure 1103, or table base 1104. The descriptions above with reference to FIG. 11D also applies to the mechanical grounding options illustrated in FIG. 11F. Computer-assisted device 1151 and surgical table 1100 work together as described herein.

Figure 11G:
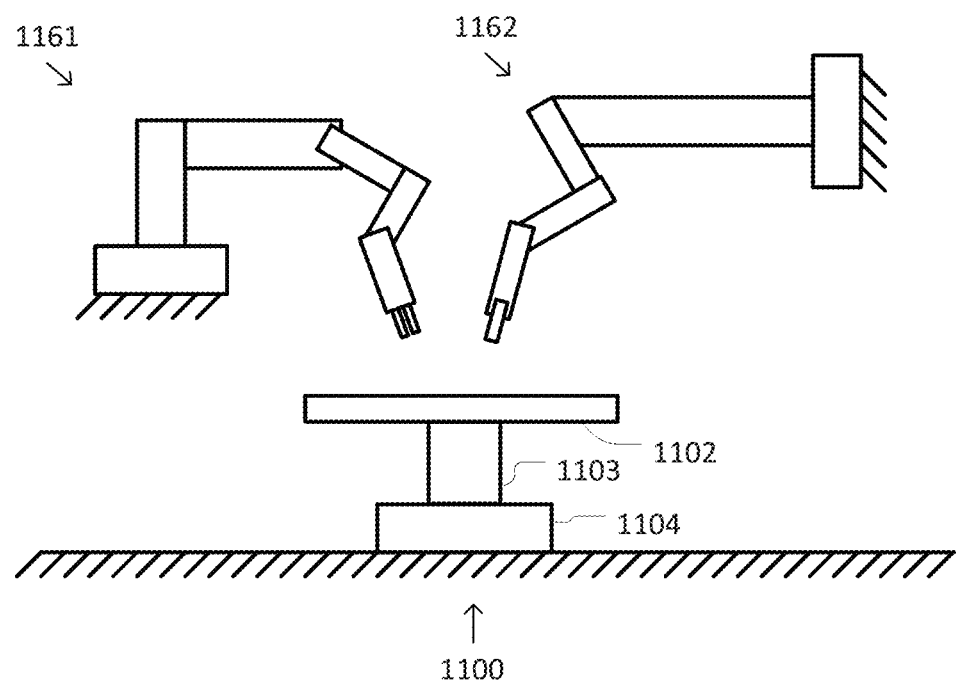

FIG. 11G illustrates that one or more teleoperated multi-instrument, single-body opening computer-assisted devices 1161 and one or more teleoperated single-instrument computer-assisted devices 1162 may be combined to operate with surgical table 1100 as described herein. Each of the computer-assisted devices 1161 and 1162 may be mechanically grounded, directly or via another structure, in various ways as described above.

Figure 3:
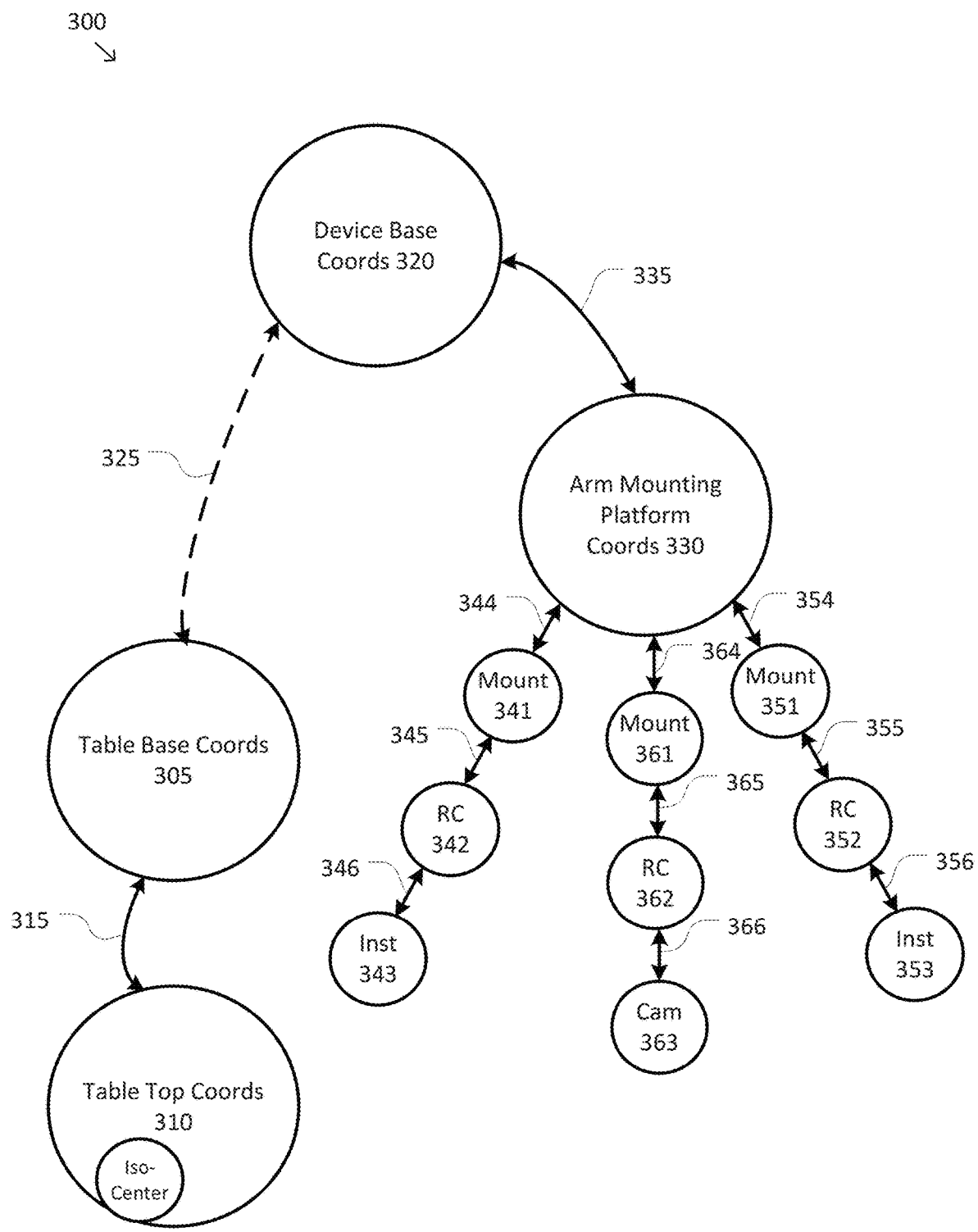
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. The kinematic information is based on known kinematic models for the links and joints of a computer-assisted medical device and a surgical table. The kinematic information is further based on information associated with the position and/or orientation of the joints of the computer-assisted medical device and the surgical table. In some examples, the information associated with the position and/or orientation of the joints may be derived from one or more sensors, such as encoders, measuring the linear positions of prismatic joints and the rotational positions of revolute joints.

The kinematic model 300 includes several coordinate frames or coordinate systems and transformations, such as homogeneous transforms, for transforming positions and/or orientation from one of the coordinate frames to another of the coordinate frames. In some examples, the kinematic model 300 may be used to permit the forward and/or reverse mapping of positions and/or orientations in one of the coordinate frames in any other of the coordinate frames by composing the forward and/or reverse/inverse transforms noted by the transform linkages included in FIG. 3. In some examples, when the transforms are modeled as homogenous transforms in matrix form, the composing is accomplished using matrix multiplication. In some embodiments, the kinematic model 300 may be used to model the kinematic relationships of the computer-assisted device 210 and the surgical table 280 of FIG. 2.

The kinematic model 300 includes a table base coordinate frame 305 that is used to model a position and/or orientation of a surgical table, such as surgical table 170 and/or surgical table 280. In some examples, the table base coordinate frame 305 may be used to model other points on the surgical table relative to a reference point and/or orientation associated with the surgical table. In some examples, the reference point and/or orientation may be associated with a table base of the surgical table, such as the table base 282. In some examples, the table base coordinate frame 305 may be suitable for use as a world coordinate frame for the computer-assisted system.

The kinematic model 300 further includes a table top coordinate frame 310 that may be used to model positions and/or orientations in a coordinate frame representative of a table top of the surgical table, such as the table top 284. In some examples, the table top coordinate frame 310 may be centered about a rotational center or isocenter of the table top, such as isocenter 286. In some examples, the z-axis of the table top coordinate frame 310 may be oriented vertically with respect to a floor or surface on which the surgical table is placed and/or orthogonal to the surface of the table top. In some examples, the x- and y-axes of the table top coordinate frame 310 may be oriented to capture the longitudinal (head to toe) and lateral (side-to-side) major axes of the table top. In some examples, a table base to table top coordinate transform 315 is used to map positions and/or orientations between the table top coordinate frame 310 and the table base coordinate frame 305. In some examples, one or more kinematic models of an articulated structure of the surgical table, such as articulated structure 290, along with past and/or current joint sensor readings is used to determine the table base to table top coordinate transform 315. In some examples consistent with the embodiments of FIG. 2, the table base to table top coordinate transform 315 models the composite effect of the height, tilt, Trendelenburg, and/or slide settings associated with the surgical table.

The kinematic model 300 further includes a device base coordinate frame that is used to model a position and/or orientation of a computer-assisted device, such as computer-assisted device 110 and/or computer-assisted device 210. In some examples, the device base coordinate frame 320 may be used to model other points on the computer-assisted device relative to a reference point and/or orientation associated with the computer-assisted device. In some examples, the reference point and/or orientation may be associated with a device base of the computer-assisted device, such as the mobile cart 215. In some examples, the device base coordinate frame 320 may be suitable for use as the world coordinate frame for the computer-assisted system.

In order to track positional and/or orientational relationships between the surgical table and the computer-assisted device, it is often desirable to perform a registration between the surgical table and the computer-assisted device. As shown in FIG. 3, the registration may be used to determine a registration transform 325 between the table top coordinate frame 310 and the device base coordinate from 320. In some embodiments, the registration transform 325 may be a partial or full transform between the table top coordinate frame 310 and the device base coordinate frame 320. The registration transform 325 is determined based on the architectural arrangements between the surgical table and the computer-assisted device.

In the examples of FIGS. 11D and 11F, where the computer-assisted device is mounted to the table top 1102, the registration transform 325 is determined from the table base to table top coordinate transform 315 and knowing where the computer-assisted device is mounted to the table top 112.

In the examples of FIGS. 11A-11C, 11E, and 11F, where the computer-assisted device is placed on the floor or mounted to the wall or ceiling, determination of the registration transform 325 is simplified by placing some restrictions on the device base coordinate frame 320 and the table base coordinate frame 305. In some examples, these restrictions include that both the device base coordinate frame 320 and the table base coordinate frame 305 agree on the same vertical up or z-axis. Under the assumption that the surgical table is located on a level floor, the relative orientations of the walls of the room (e.g., perpendicular to the floor) and the ceiling (e.g., parallel to the floor) are known it is possible for a common vertical up or z axis (or a suitable orientation transform) to be maintained for both the device base coordinate frame 320 and the table base coordinate frame 305 or a suitable orientation transform. In some examples, because of the common z-axis, the registration transform 325 may optionally model just the rotational relationship of the device base to the table base about the z-axis of the table base coordinate frame 305 (e.g., a $\theta_Z$ registration). In some examples, the registration transform 325 may optionally also model a horizontal offset between the table base coordinate frame 305 and the device base coordinate frame 320 (e.g., a XY registration). This is possible because the vertical (z) relationship between the computer-assisted device and the surgical table are known. Thus, changes in a height of the table top in the table base to table top transform 315 are analogous to vertical adjustments in the device base coordinate frame 320 because the vertical axes in the table base coordinate frame 305 and the device base coordinate frame 320 are the same or nearly the same so that changes in height between the table base coordinate frame 305 and the device base coordinate frame 320 are within a reasonable tolerance of each other. In some examples, the tilt and Trendelenburg adjustments in the table base to table top transform 315 may be mapped to the device base coordinate frame 320 by knowing the height of the table top (or its isocenter) and the Oz and/or XY registration. In some examples, the registration transform 325 and the table base to table top transform 315 may be used to model the computer-assisted surgical device as if it were attached to the table top even when this is architecturally not the case.

The kinematic model 300 further includes an arm mounting platform coordinate frame 330 that is used as a suitable model for a shared coordinate frame associated with the most proximal points on the articulated arms of the computer-assisted device. In some embodiments, the arm mounting platform coordinate frame 330 may be associated with and oriented relative to a convenient point on an arm mounting platform, such as the arm mounting platform 227. In some examples, the center point of the arm mounting platform coordinate frame 330 may be located on the arm mounting platform orientation axis 236 with the z-axis of the arm mounting platform coordinate frame 330 being aligned with arm mounting platform orientation axis 236. In some examples, a device base to arm mounting platform coordinate transform 335 is used to map positions and/or orientations between the device base coordinate frame 320 and the arm mounting platform coordinate frame 330. In some examples, one or more kinematic models of the links and joints of the computer-assisted device between the device base and the arm mounting platform, such as the set-up structure 220, along with past and/or current joint sensor readings are used to determine the device base to arm mounting platform coordinate transform 335. In some examples consistent with the embodiments of FIG. 2, the device base to arm mounting platform coordinate transform 335 may model the composite effect of the two-part column, shoulder joint, two-part boom, and wrist joint of the setup structure portion of the computer-assisted device.

The kinematic model 300 further includes a series of coordinate frames and transforms associated with each of the articulated arms of the computer-assisted device. As shown in FIG. 3, the kinematic model 300 includes coordinate frames and transforms for three articulated arms, although one of ordinary skill would understand that different computer-assisted devices may include fewer and/or more articulated arms (e.g., one, two, four, five, or more). Consistent with the configuration of the links and joints of the computer-assisted device 210 of FIG. 2, each of the articulated arms is modeled using a manipulator mount coordinate frame, a remote center of motion coordinate frame, and an instrument or camera coordinate frame, depending on a type of instrument mounted to the distal end of the articulated arm.

In the kinematic model 300, the kinematic relationships of a first one of the articulated arms is captured using a manipulator mount coordinate frame 341, a remote center of motion coordinate frame 342, an instrument coordinate frame 343, an arm mounting platform to manipulator mount transform 344, a manipulator mount to remote center of motion transform 345, and a remote center of motion to instrument transform 346. The manipulator mount coordinate frame 341 represents a suitable model for representing positions and/or orientations associated with a manipulator, such as manipulator 260. The manipulator mount coordinate frame 341 is associated with a manipulator mount, such as the manipulator mount 262 of the corresponding articulated arm. The arm mounting platform to manipulator mount transform 344 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 342 is associated with a remote center of motion of the instrument mounted on the manipulator, such as the corresponding remote center of motion 274 of the corresponding manipulator 260. The manipulator mount to remote center of motion transform 345 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the manipulator mount to remote center of motion transform 345 includes an essentially static translational component that does not change as the manipulator and instrument are operated and a dynamic rotational component that changes as the manipulator and instrument are operated.

The instrument coordinate frame 343 is associated with an end effector located at the distal end of the instrument, such as the corresponding end effector 276. The remote center of motion to instrument transform 346 is then based on one or more kinematic models of the links and joints of the computer-assisted device that move and/or orient the corresponding instrument, end effector, and remote center of motion, along with past and/or current joint sensor readings. In some examples, the remote center of motion to instrument transform 346 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 346 may be constrained to reflect that the insertion axis of the shaft of the instrument passes through the remote center of motion and accounts for rotations of the shaft and the end effector about the axis defined by the shaft.

In the kinematic model 300, the kinematic relationships of a second one of the articulated arms is captured using a manipulator mount coordinate frame 351, a remote center of motion coordinate frame 352, an instrument coordinate frame 353, an arm mounting platform to manipulator mount transform 354, a manipulator mount to remote center of motion transform 355, and a remote center of motion to instrument transform 356. The manipulator mount coordinate frame 351 represents a suitable model for representing positions and/or orientations associated with a manipulator, such as manipulator 260. The manipulator mount coordinate frame 351 is associated with a manipulator mount, such as the manipulator mount 262 of the corresponding articulated arm. The arm mounting platform to manipulator mount transform 354 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 352 is associated with a remote center of motion of the manipulator mounted on the articulated arm, such as the corresponding remote center of motion 274 of the corresponding manipulator 260. The manipulator mount to remote center of motion transform 355 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 355 includes an essentially static translational component that does not change as the manipulator and instrument are operated and a dynamic rotational component that changes as the manipulator and instrument are operated.

The instrument coordinate frame 353 is associated with an end effector located at the distal end of the instrument, such as the corresponding instrument 270 and/or end effector 276. The remote center of motion to instrument transform 356 is then based on one or more kinematic models of the links and joints of the computer-assisted device that move and/or orient the corresponding instrument, end effector, and remote center of motion, along with past and/or current joint sensor readings. In some examples, the remote center of motion to instrument transform 356 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 356 may be constrained to reflect that the insertion axis of the shaft of the instrument passes through the remote center of motion and accounts for rotations of the shaft and the end effector about the insertion axis defined by the shaft.

In the kinematic model 300, the kinematic relationships of a third one of the articulated arms is captured using a manipulator mount coordinate frame 361, a remote center of motion coordinate frame 362, a camera coordinate frame 363, an arm mounting platform to manipulator mount transform 364, a manipulator mount to remote center of motion transform 365, and a remote center of motion to camera transform 366. The manipulator mount coordinate frame 361 represents a suitable model for representing positions and/or orientations associated with a manipulator, such as manipulator 260. The manipulator mount coordinate frame 361 is associated with a manipulator mount, such as the manipulator mount 262 of the corresponding articulated arm. The arm mounting platform to manipulator mount transform 364 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 362 is associated with a remote center of motion of the manipulator mounted on the articulated arm, such as the corresponding remote center of motion 274 of the corresponding manipulator 260. The manipulator mount to remote center of motion transform 365 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 365 includes an essentially static translational component that does not change as the manipulator and instrument are operated and a dynamic rotational component that changes as the manipulator and instrument are operated.

The camera coordinate frame 363 is associated with an imaging device, such an endoscope, mounted on the articulated arm. The remote center of motion to camera transform 366 is then based on one or more kinematic models of the links and joints of the computer-assisted device that move and/or orient the imaging device and the corresponding remote center of motion, along with past and/or current joint sensor readings. In some examples, the remote center of motion to camera transform 366 accounts for the orientation at which the shaft, such as the corresponding shaft 272, passes through the remote center of motion and the distance to which the shaft is advanced and/or withdrawn relative to the remote center of motion. In some examples, the remote center of motion to camera transform 366 may be constrained to reflect that the insertion axis of the shaft of the imaging device passes through the remote center of motion and accounts for rotations of the imaging device about the axis defined by the shaft.

As discussed above and further emphasized here, FIG. 3 is merely an example which should not unduly limit the scope of the claims. One of ordinary skill in the art would recognize many variations, alternatives, and modifications. According to some embodiments, the registration between the surgical table and the computer-assisted device may be determined between the table top coordinate frame 310 and the device base coordinate frame 320 using an alternative registration transform. When the alternative registration transform is used, registration transform 325 is determined by composing the alternative registration transform with the inverse/reverse of the table base to table top transform 315. According to some embodiments, the coordinate frames and/or transforms used to model the computer-assisted device may be arranged differently dependent on the particular configuration of the links and joints of the computer-assisted device, its articulated arms, its end effectors, its manipulators, and/or its instruments. According to some embodiments, the coordinate frames and transforms of the kinematic model 300 may be used to model coordinate frames and transforms associated with one or more virtual instruments and/or virtual cameras. In some examples, the virtual instruments and/or cameras may be associated with previously stored and/or latched instrument positions, projections of instruments and/or cameras due to a motion, reference points defined by a surgeon and/or other personnel, and/or the like.

As described previously, as a computer-assisted system, such as computer-assisted systems 100 and/or 200, is being operated, it would be desirable to allow continued control of the instruments and end effectors using the computer-assisted device while motion of a surgical table, such as surgical tables 170 and/or 280, is allowed. In some examples, this allows for a less time-consuming procedure as surgical table motion occurs without having to first remove instruments and end effectors from the patient or disconnect instruments, which remain inside the patient, from the manipulators coupling the instruments to the computer-assisted device before letting the surgical table move. In some examples, this may optionally allow a surgeon and/or other medical personnel to monitor organ movement while the surgical table motion is occurring to obtain a more optimal surgical table pose. In some examples, this may also optionally permit active continuation of a surgical procedure during surgical table motion.

Figure 4:
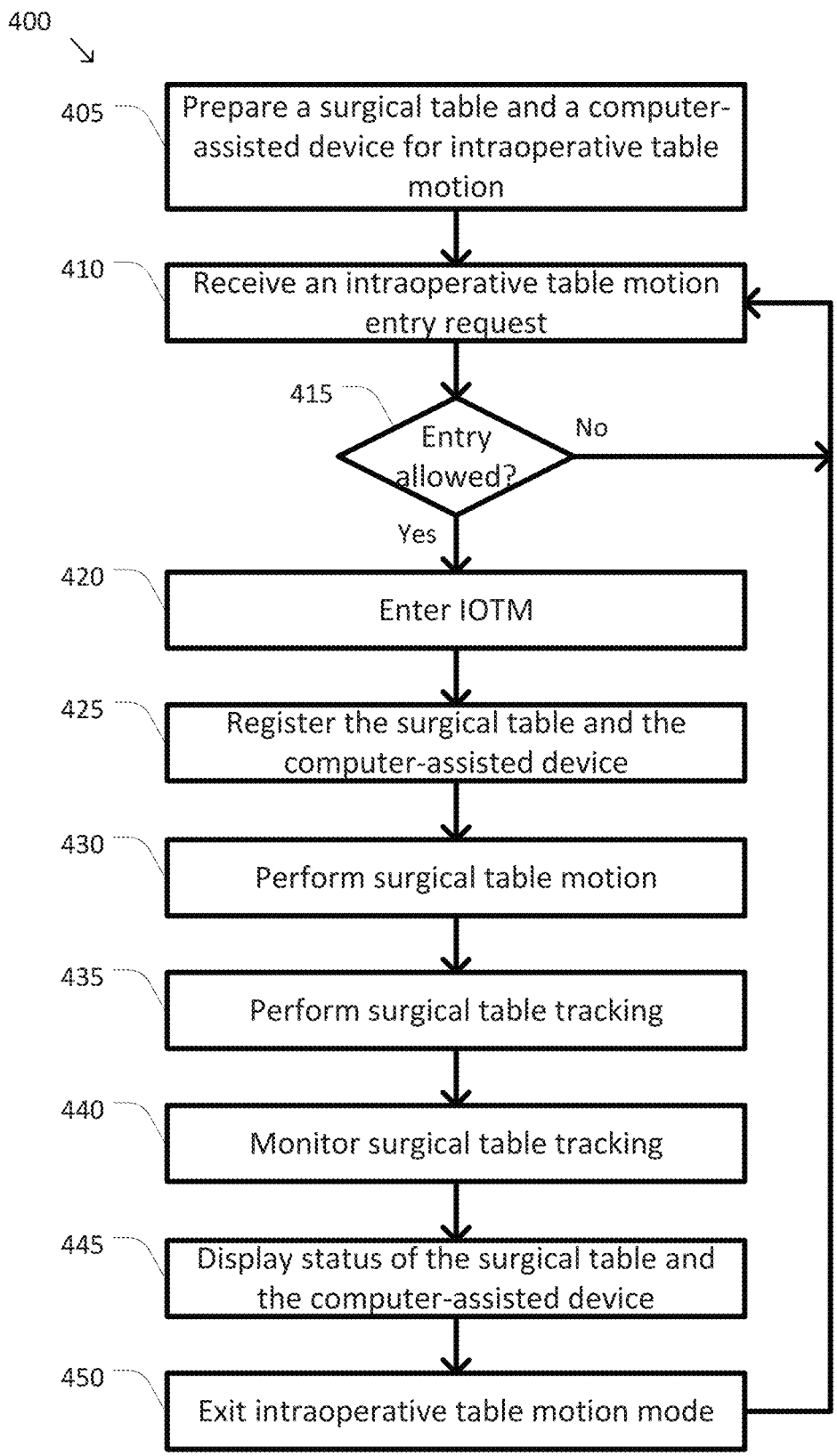
FIG. 4 is a simplified diagram of the method of integrated surgical table motion according to some embodiments.

FIG. 4 is a simplified diagram of the method 400 of integrated surgical table motion according to some embodiments. One or more of the processes 405-450 of method 400 may be implemented, at least in part, in the form of executable code stored on non-transient, tangible, machine readable media that when run by one or more processors (e.g., the processor 140 in control unit 130) may cause the one or more processors to perform one or more of the processes 405-450. In some embodiments, method 400 may be used to allow surgical table motion to occur without first having to remove instruments and end effectors from the patient or disconnect instruments, which remain inside the patient, from the manipulators coupling the instruments to the computer-assisted device before letting the surgical table move. While one or more manipulators of a computer-assisted device are docked to a patient and/or one or more corresponding instruments are within the interior of the patient's anatomy. In some examples, this may optionally allow a surgeon and/or other medical personnel to monitor organ movement while the surgical table motion is occurring to obtain a more optimal surgical table pose. In some examples, this may also optionally permit active continuation of a surgical procedure during surgical table motion. According to some embodiments, the order in which processes 405-450 are performed may optionally vary from the order implied by the diagram of FIG. 4. In some examples, the registering of process 425 may optionally be performed before or concurrently with processes 405, 410, and/or 405. In some examples, the registering of process 425 may be performed and/or repeated concurrently with processes 430-445. In some examples, processes 430-445 may be performed concurrently.

At a process 405, a surgical table and a computer-assisted device are prepared for intraoperative table motion. In some embodiments, various preparation steps are generally performed before a surgical table, such as surgical table 170 and/or 280, and a computer-assisted device, such as computer assisted device 110 and/or 210, are used in an integrated fashion where motion of the surgical table is permitted while instruments of the computer-assisted device are inserted into a patient.

Figure 5:
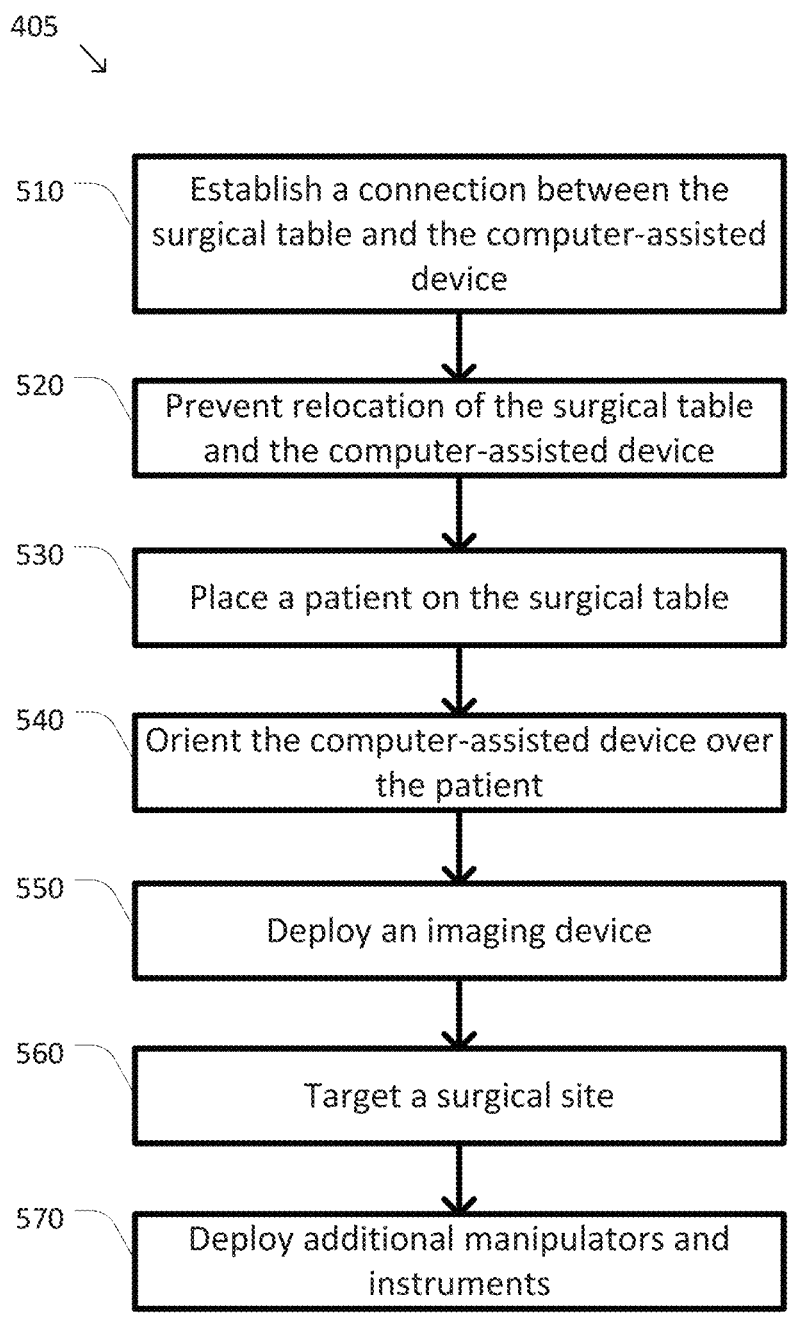
FIG. 5 is a simplified diagram of a process for preparing a surgical table and a computer-assisted device for intraoperative table motion according to some embodiments.

FIG. 5 is a simplified diagram of the process 405 for preparing a surgical table and a computer-assisted device for intraoperative table motion according to some embodiments. One or more of the processes 510-570 of process 405 may be implemented, at least in part, in the form of executable code stored on non-transient, tangible, machine readable media that when run by one or more processors (e.g., the processor 140 in control unit 130) may cause the one or more processors to perform one or more of the processes 510-570. In some embodiments, process 405 may be used to prepare and/or configure the surgical table and the computer-assisted device so that surgical table motion may occur while one or more instruments of the computer-assisted device are inserted into the patient and/or one or more corresponding instruments are within the interior of the patient's anatomy. According to some embodiments, the order in which processes 510-570 are performed may optionally vary from the order implied by the diagram of FIG. 5. In some examples, the preventing of the relocation of the surgical table and the computer-assisted device of process 520 may optionally be performed before, during or after any of the processes 510-540. For example, the patient could be placed on the surgical table and/or the computer-assisted device oriented over the patient before the preventing of the relocation occurs in process 520.

At a process 510, a connection is established between the surgical table and the computer-assisted device. To provide appropriate safety during intraoperative table motion, the computer-assisted device is operating in a supervisory capacity over the surgical table so that motion of the surgical table is not performed without authorization from the computer-assisted device. In order to provide supervision over the surgical table, a communication connection is established between the surgical table and the computer-assisted device. In some examples, the communication connection may correspond to the interface between surgical table 170 and the control unit 130 as described in the embodiments of FIG. 1. In some examples, the connection may include an infrared proximity detection system to help verify that the surgical table and the computer-assisted device are in suitable proximity to each other. In some examples, suitable infrared emitters and/or detectors may be installed on a base of the surgical table and a base of the computer-assisted device in locations where they are not likely to be obscured by other equipment in a surgical room and/or interventional suite and/or by medical personnel. As the infrared emitters and detectors are moved into range with each other, various identifiers, keys, and/or messages may be exchanged that allow the surgical table and the computer-assisted device to confirm that they are each in proximity to a compatible device supporting intraoperative table motion and are able to establish an on-going connection. In some examples, the messages may optionally include messages for coordinating the connection, messages for surgical table motion requests, messages for approving surgical table motion requests, messages for exchanging status and/or kinematic information, and/or the like. In some examples, a wireless connection based on radio frequency signals, near field communication, and/or the like may optionally be used as a replacement and/or a supplement to the infrared proximity detection system. In some examples, one or more cables may optionally be coupled between corresponding communication ports on the surgical table and the computer-assisted device as a replacement and/or a supplement to the infrared proximity detection system or other communication system. In some examples, the one or more cables may replace and/or provide redundancy in the establishment of the connection. In some embodiments, the connection may additionally include one or more mechanical devices to aid in the registration between the surgical table and the computer-assisted device as is described in further detail below.

At a process 520, relocation of the surgical table and the computer-assisted device is prevented. Because both the surgical table and the computer-assisted device have limited range of motion, and in order to help maintain registration between the surgical table and the computer-assisted device, relative location of both the surgical table and the computer-assisted device is prevented during intraoperative table motion. Thus, at some point before allowing the surgical table and the computer-assisted device to enter an intraoperative table motion mode (see process 420 below), further relocation of the surgical table and the computer-assisted device is prevented. In some examples, this may also prevent relative motion between the base of the surgical table and the base of the computer-assisted device. In some embodiments, relocation of the surgical table and the computer-assisted device may be prevented by locking one or more feet, wheels, and/or mounting clamps of the base of the surgical table or the base of the computer-assisted device so that neither the surgical table nor the base of the computer-assisted device may be rolled across the floor, moved along the wall, or moved along the ceiling of the surgical room and/or interventional suite and/or moved along the table top during intraoperative table motion. In some examples, the feet, wheels, and/or mounting clamps of the computer-assisted device may be automatically locked when a cannula is mounted to one or more of the manipulators or instruments. In some examples, the status of the feet, wheel, and/or mounting clamp locks are monitored, using one or more sensors, throughout intraoperative table motion. In some examples, when loss of feet, wheel, and/or mounting clamp lock is detected, this may result in premature termination of intraoperative table motion. In some examples, movement of either the base of the surgical table and/or the base of the computer-assisted device may be determined by monitoring sequence numbers associated with corresponding feet, wheels, or mounting clamps. In some examples, sequence numbers tracking the number of times each of the feet, wheel, and mounting clamp locks are engaged and/or disengaged may be used to determine one or more temporary losses of lock. Rotational encoders and/or rotational counters associated with each wheel may be monitored to detect rotation of any one of the wheels. Changes in any of the sequence numbers provide an indication that relocation of the base of the surgical table and/or the base of the computer-assisted device has or is occurring.

At a process 530, a patient is placed on the surgical table. In some examples, hospital and/or recommended medical practices may be used to place the patient on the surgical table, secure the patient to the surgical table, and verify that the patient is properly secure. In some examples, placing the patient on the surgical table may further include leveling the top of the table by, for example, adjusting tilt and/or Trendelenburg settings to a neutral zero degrees. In some examples, the patient may be centered on the top of the table and/or a slide of the table may be adjusted to center the top of the table over the articulated structure of the surgical table. In some examples, a height of the table may also be adjusted. In some examples, an isocenter of the surgical table, such as isocenter 286, may be optionally adjusted to a point above the top of the surgical table that approximately corresponds to an intended surgical site. In some examples, this point may be located about 35 cm above the top of the surgical table. In some examples, the isocenter 286 may be collocated with the body wall of the patient at or near one of the body openings, such as an incision site or body orifice, corresponding to remote center of motion 274. In some examples, locating the isocenter at or near one or more of the remote centers of motion and/or the intended surgical site may reduce the amount of surgical table motion that has to be compensated for by the computer-assisted device when Trendelenburg adjustments are made to the surgical table.

At a process 540, the computer-assisted device is oriented over the patient. To allow for adequate range of motion during a procedure, the articulated arms, end effectors, and/or manipulators of the computer-assisted device are positioned and oriented over the patient based on the desired surgical site. In some examples, this may include adjusting one or more joints in a set-up structure and/or set-up joints of the computer-assisted device so that instruments, end effectors, and/or manipulators are positioned above and around the desired surgical site. Consistent with the embodiments of FIG. 2, this orientation may include centering the arm mounting platform 227 over the desired surgical site, rotating the arm mounting platform 227 so that the articulated arms mounted to the arm mounting platform 227 are arrayed about the desired surgical site, and/or adjusting a height of the arm mounting platform 227. A more thorough discussion of possible goals and/or operations used to perform this orientation are described in greater detail in U.S. Provisional Patent Application No. 62/024,887 entitled "System and Method for Aligning with a Reference Target," which was filed on Jul. 15, 2014, U.S. Provisional Patent Application No. 61/954,261 entitled "System and Method for Aligning with a Reference Target," which was filed on Mar. 17, 2014, and PCT Patent Application No. PCT/US15/21089 entitled "System and Method for Maintaining a Tool Pose," which was filed on Mar. 17, 2015, each of which are hereby incorporated by reference.

At a process 550, an imaging device is deployed. To provide the surgeon and/or other medical personnel with images of the surgical site, an imaging device may be docked to the patient. In some examples, an incision may be made in the patient and a cannula inserted through the exterior anatomy of the patient, such as through the abdominal wall. The cannula is then attached to a distal end of one of the manipulators, such as the manipulator corresponding to the remote center of motion coordinate frame 362. An imaging device, such as an endoscope, may be mounted as an instrument to the manipulator and then inserted through the cannula to obtain interior images of the patient's anatomy.

At a process 560, the desired surgical site is targeted. Once the imaging device is inserted through the cannula, one or more joints in the set-up joints and/or the manipulator to which the imaging device is mounted are adjusted to orient the imaging device. The imaging device is then oriented so that it has a viewing direction toward the desired surgical site and a viewing direction axis of a corresponding camera coordinate frame, such as camera coordinate frame 363, is oriented in the same direction. The imaging device may also be inserted and/or retracted to a desired working depth. In some examples, the imaging device may also be rotated to provide a suitable view up orientation in captured images and the corresponding camera coordinate frame. In some examples, one or more of the joints in the set-up joints and/or the manipulator may be placed in an unlocked state to allow medical personnel to manually adjust the orientation of the imaging device. In some embodiments, once the desired surgical site is targeted, additional adjustments may be made to the computer-assisted device to better orient the computer-assisted device over the patient. In some examples, an alignment procedure, such as the alignment procedure described in greater detail in U.S. Provisional Patent Application No. 62/024,887 entitled "System and Method for Aligning with a Reference Target," which was filed on Jul. 15, 2014, U.S. Provisional Patent Application No. 61/954,261 entitled "System and Method for Aligning with a Reference Target," which was filed on Mar. 17, 2014, and PCT Patent Application No. PCT/US15/21089 entitled "System and Method for Maintaining a Tool Pose," which was filed on Mar. 17, 2015, each of which are hereby incorporated by reference, may be used.

At an optional process 570, additional manipulators and instruments may be deployed. Using a process similar to process 550, one or more additional instruments may be mounted to corresponding manipulators and inserted into the patient using corresponding cannulas. The end effectors of the instruments are then placed in a suitable pose for the current procedure.

Referring back to FIG. 4, at a process 410, an intraoperative table motion entry request is received. In some examples, entry into the intraoperative table motion mode is made by express request from medical personnel operating the surgical table and/or the computer-assisted device. In some examples, medical personnel operating the computer-assisted device may request intraoperative table motion entry using one or more input controls on an operator workstation, such as a pedal, switch, button, graphical user interface control, and/or the like. In some examples, medical personnel operating the surgical table, such as an anesthesiologist, may request intraoperative table motion entry using one or more surgical table controls, such as a button on a surgical table command unit for the surgical table. In some examples, the intraoperative table motion entry request may be received as one or more messages received over the connection between the surgical table and the computer-assisted device and/or one or more messages received by a system control unit, such as control unit 130. In some examples, the intraoperative table motion entry request may occur automatically in response to establishment of the connection between the surgical table and the computer-assisted device and detection that at least one instrument has been mounted to a manipulator and has been inserted into a patient.

Figure 6:
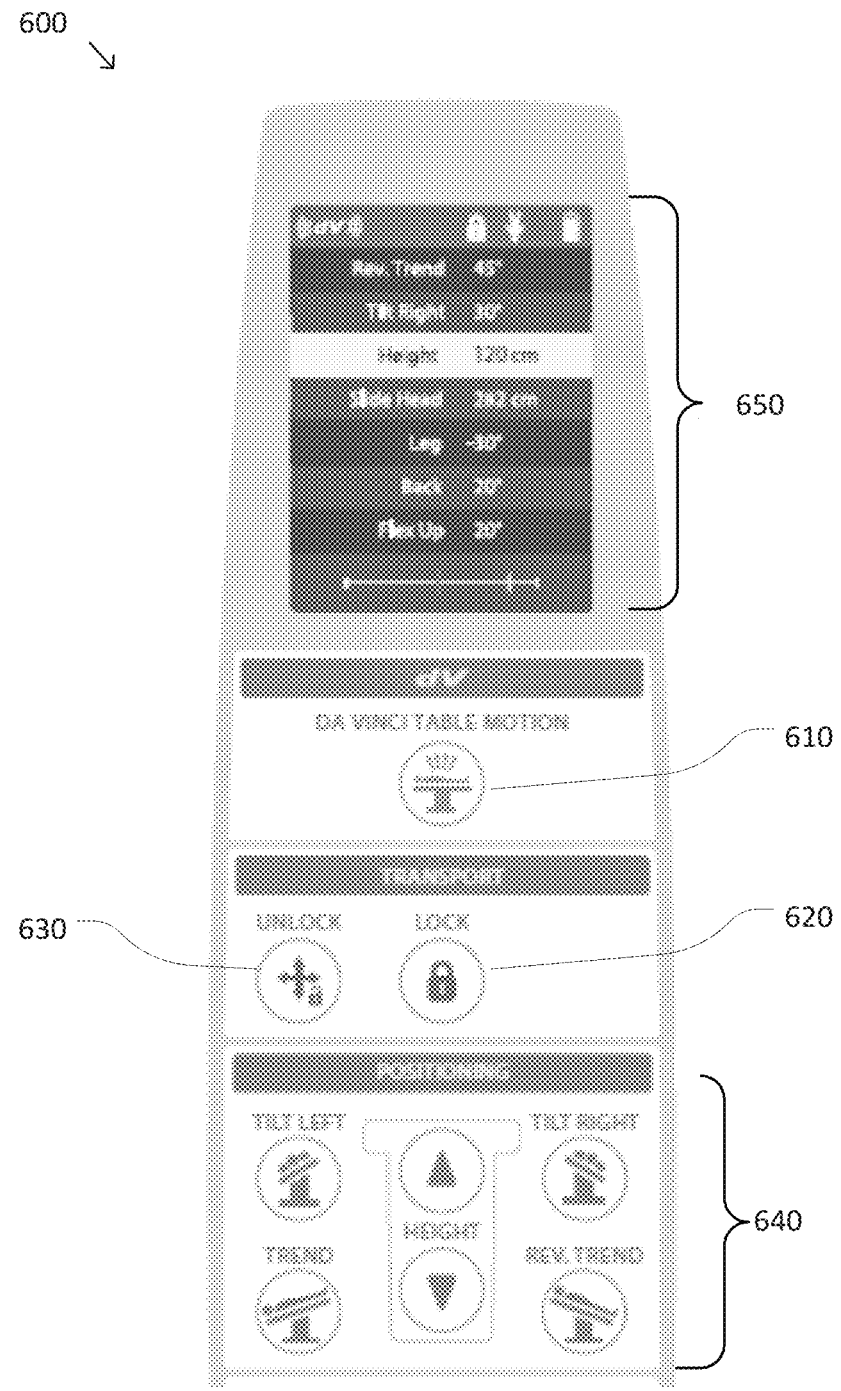
FIG. 6 is a simplified diagram of a portion of a surgical table command unit according to some embodiments.

FIG. 6 is a simplified diagram of a portion of a surgical table command unit 600 according to some embodiments. As shown in FIG. 6, the surgical table command unit 600 may be of a size and shape similar to a remote control used commonly with consumer electronic devices such as televisions, digital video recorders, and/or the like. In some examples, the surgical table command unit 600 may be coupled to the surgical table using a cable to support communication between the surgical table command unit 600 and the controllers, electronics, and/or processors in the surgical table. In some examples, the surgical table command unit 600 may alternatively be coupled to the surgical table using a wireless interface, such an infrared, radio frequency, and/or near field interface. Surgical table command unit 600 is divided into various regions, with each region providing input buttons and/or status information. In some examples, illumination of each of the buttons may be optionally manipulated to indicate which of the buttons are available to input surgical table motion commands. For example, active buttons that are available are illuminated and inactive buttons that are not available are not illuminated. In some examples, a color of illumination, such as green for active and red for inactive, may optionally be used instead of removing illumination from inactive buttons.

Surgical table command unit 600 includes an optional intraoperative table motion entry button 610. An operator of surgical table command unit 600 may use intraoperative table motion entry button 610 to enter and/or exit intraoperative table motion mode. When surgical table command unit 600 is used during method 400, pressing intraoperative table motion entry button 610 may trigger the intraoperative table motion entry request that is received during process 410. In some examples, intraoperative table motion entry button 610 may be controllably illuminated to indicate whether conditions are suitable for intraoperative table motion as is discussed in further detail below with respect to process 415.

Surgical table command unit 600 may further include a transport lock button 620 and an unlock button 630 that may be used to control locking of the feet and/or wheels of the surgical table. In some examples, lock button 620 may be used during process 520 to enable locking of the feet and/or wheels of the surgical table. In some examples, lock button 620 may be illuminated when the feet and/or wheels of the surgical table are locked. In some examples, unlock button 630 may be deactivated when the surgical table and the computer-assisted device are in intraoperative table motion mode.

Surgical table command unit 600 further includes several movement request buttons 640. The movement request buttons 640 may be used to make surgical table movement requests in intraoperative table motion as well as other operating modes of the surgical table. As shown in FIG. 6, the movement request buttons 640 includes buttons for tilting the top of the surgical table left or right, adjusting the Trendelenburg setting for the surgical table, and adjusting the height of the top of the surgical table relative to the floor. Depending upon the operating mode of the surgical table and/or whether range of motion limits are reached, each of the movement request buttons 640 may be controllably illuminated to indicate whether the respective movement request button 640 is active. For example, when the surgical table is extended to its full height, illumination may be removed from the height up button. Although not shown in FIG. 6, additional movement request buttons may be included on surgical table command unit 600, such as buttons for controlling longitudinal slide, head up, head down, feet up, feet down, and/or the like.

Surgical table command unit 600 further includes a status display region 650. Status display region 650 includes a multi-line display and/or a raster display for indicating status and/or settings of the surgical table. The status display region 650 may include one or more lines of status information and/or one or more status icons. In the examples, of FIG. 6, the status display region 650 includes status icons for intraoperative table motion status, feet/wheel/mounting clamp locking, communication connection, and power as well as status lines indicating the current settings for Trendelenburg orientation, tilt, height, slide, leg, back, and/or the like.

Although not shown in FIG. 6, surgical table command unit 600 may include additional buttons and/or status display regions. In some examples, the additional buttons may include buttons for controlling power to the surgical table, auto-leveling the surgical table, disconnecting the surgical table from the computer-assisted device, and/or the like.

Referring back to FIG. 4, at a process 415 it is determined whether intraoperative table motion is allowed. To provide suitable safety in the operation of the surgical table and the computer-assisted devices, several safety interlocks and/or checks are performed before entry into intraoperative table motion is permitted. In some examples, the checks may include verifying that each of the processes 510-570 have been performed. This may, for example, include verifying that both the surgical table and the computer-assisted device have been initialized, the feet, wheels, and/or mounting clamps of both the surgical table and the computer-assisted device are locked, and that at least one instrument has been mounted to a manipulator and inserted into the patient.

In some embodiments, additional optional checks may also be performed. In some examples, the additional checks may include verifying that a surgeon and/or other personnel are present at the operator console. In some examples, this includes confirming that any appropriate interlocks, such as a head-in sensor on a monitor displaying images from an imaging device docked to the patient, indicates that an operator is present to visually supervise motion of the instruments inserted into the patient. In some examples, the additional checks may include verifying that the end effectors of instruments that are mounted to manipulators and inserted beyond a corresponding cannula are within the field of view of the imaging device deployed during process 550. This helps ensure that the operator is able to observe any inserted instruments during intraoperative table motion. In some examples, the additional checks may include verifying that none of the joints of the computer-assisted device have been manually unlocked, such as by an operator using unlocking buttons located on the arm mounting platform 227, the set-up joints 240 and corresponding links, and/or the manipulators 260 associated with any of the instruments mounted to a manipulator and inserted into the patient. In some examples, the additional checks may include monitoring checks to determine whether one or more joints of the computer-assisted device are at or near a range of motion limit and/or whether the computer-assisted surgical device is successfully changing the pose of the instruments to compensate for surgical table motion. In some examples, the additional checks may include an assessment whether the planned procedure is on a list of procedures compatible with intraoperative table motion, whether the insertion points for the cannulas associated with the docked arms are able to provide sufficient rigidity to the cannulas to support dragging of the cannulas and instruments as the patient moves as a result of intraoperative table motion, and/or whether the instruments mounted to the manipulators are compatible with intraoperative table motion. In some examples, incompatible instruments may be instruments for cardiac, trans-oral, and/or instruments for other procedures not on the list of procedures compatible with intraoperative table motion. In some examples, the additional checks may include one or more operator-confirmed checks associated with clearance checks to determine whether the surgical table and/or the computer-assisted device have sufficient clearance for intraoperative table motion, such as obstructions due to the patient, surgical drapes, cabling, and/or the like. In some examples, the additional checks may include determining whether the articulated arms, manipulators, and/or mounted instruments are functional and/or operating without unacceptable degradation. In some examples, the additional checks may also include other system, calibration, and/or similar checks.

When intraoperative table motion is not allowed, entry into intraoperative table motion is blocked by the processor and the intraoperative table motion entry request is denied. In some examples, when intraoperative table motion is blocked, one or more informational messages, alerts, and/or the like may be issued to explain why intraoperative table motion is blocked. In some examples, once the intraoperative table motion request is denied, the method returns to process 410 until another intraoperative table motion entry request is received. When intraoperative table motion is allowed, intraoperative table motion is entered beginning with a process 420.

At the process 420, intraoperative table motion is entered. Following the receipt of the intraoperative table motion entry request during process 410 and the successful passing of the safety interlocks and/or checks of process 415, the computer-assisted device and the surgical table are allowed to begin intraoperative table motion. Because the patient may move as a result of movement by the top of the surgical table during intraoperative table motion, the remote centers of motion of the docked articulated arms may have to move as well to avoid applying too much stress to the body openings where the cannulas pass through the body wall of the patient. In some examples, in order to relieve the forces being applied to the cannulas by the body wall of the patient, the computer-assisted device is placed in a mode where one or more joints in the set-up joints and/or manipulators, of each of the articulated arms having instruments that are inserted into the patient through a body opening, are released and/or unlocked to allow for the corresponding remote centers of motion to move. In some examples, when the effective mass of the articulated arms and/or the friction in the released and/or unlocked joints is small enough, the body wall of the patient is able to apply sufficient force to cannulas so that the remote centers of motion move with the patient by dragging the cannulas through which the instruments are inserted as well as the corresponding manipulator and set-up joints using what is sometimes called "instrument dragging". Thus, as a prerequisite to instrument dragging, one or more of the joints in each of the set-up joints and/or manipulators of each of the mounted instruments that are inserted into the patient is released and/or unlocked. In some examples, a gravity or mass compensation mode is optionally used where movements in the joints of the set-up joints, manipulators, and/or instruments are tracked during instrument dragging and corresponding joint motions are introduced to create the effect that the set-up joints, manipulators, and instruments are massless or nearly massless.

It is often the case that the body wall of the patient is already applying asserted and/or pent up forces on the cannulas of the inserted instruments even before surgical table movement begins. In some examples, these pent up forces may occur when the remote centers of motion of the these instruments are not well collocated with the corresponding body openings, as a result of errors in the control of the kinematics of the instruments, motions in the patient not due to surgical table motion, changes in insufflation of the patient, stresses caused by earlier manipulator and/or instrument motion, and/or the like. Thus, when the joints are released and/or unlocked, the instrument dragging may induce an undesirable motion in the instruments and/or end effectors to relieve the pent up forces. When the undesirable motion is sufficiently large, it may result in injury to the patient and/or damage to the computer-assisted device. In some examples, the undesirable motion may be significantly reduced by monitoring the remote centers of motion and/or the end effectors as the joints are released and/or unlocked and applying compensating motions using other joints of the set-up joints and/or manipulators. In some embodiments, the undesirable motion may be significantly reduced while also optionally permitting continued manipulation of one or more of the instruments and end effectors by the operator at the operator console using the techniques described in more detail in U.S. Provisional Patent Application No. 62/134,212 entitled "System and Method for Reducing Tool Disturbances," which was filed Mar. 17, 2015, and concurrently filed PCT Patent Application No. PCT/US2015/057669 entitled "System and Method for Instrument Disturbance Compensation" and published as WO2016/069659 A1, both of which are hereby incorporated by reference in their entirety. In some examples, the amount of undesirable motion may also be reduced into a series of smaller disturbances by staggering and/or carefully controlling the order and/or timing of the release and/or unlocking of the joints as is described in further detail in U.S. Provisional Patent Application No. 62/134,225 entitled "System and Method for Reducing Tool Disturbances," which was filed Mar. 17, 2015, and concurrently filed PCT Patent Application No. PCT/US2015/057671 entitled "Medical Device with Active Brake Release Control" and published as WO2016/069661 A1, both of which are hereby incorporated by reference in their entirety.

According to some embodiments, to help support intraoperative table motion one or more kinematic relationships of the surgical table and/or the computer-assisted device, such as the transforms of FIG. 3, are recorded and/or latched prior to entry into intraoperative table motion to provide a baseline record of the positions and orientations of the manipulators, instruments, and/or end effectors before intraoperative table motion is allowed. In some examples, the kinematic relationships are recorded just before intraoperative table motion entry. In some examples, the kinematic relationships are optionally recorded whenever repositioning of the imaging device docked during process 550 is completed. As intraoperative table motion occurs, the baseline records may optionally be used to detect motion in the manipulators, instruments, and/or end effectors induced by the motion of the surgical table so that those induced motions may be automatically compensated for.

According to some embodiments, the transition period during which intraoperative table motion entry occurs is sufficiently long enough to allow for the pent up forces to be released while continuing to compensate for the undesirable motion induced by the pent up forces. In some examples, the transition period may be a few seconds in length, such as 2.5 seconds or so. In some examples, operator manipulation of the instruments and/or end effectors is optionally permitted during the intraoperative table motion entry transition period.

At a process 425, the surgical table and the computer-assisted device are registered. In order to support intraoperative table motion, it is helpful to at least partially register the surgical table and the computer-assisted device to determine the relative positioning and/or orientation between the surgical table and the computer-assisted device. As discussed above with respect to the registration transform 325, under the assumption that base coordinate frame for the surgical table and the base coordinate frame of the computer-assisted device have a common vertical up or z-axis and the height of the base of the computer-assisted device is known relative to the base of the surgical table, the registration may be characterized as determining a horizontal or x-y translation between reference points on the surgical table base and the base of the computer-assisted device and/or a rotational relationship between the surgical table base and the patient side cart. In some examples, the rotational relationship, or $\theta_Z$ registration, may account for the orientation of the base of the computer-assisted device relative to the vertical up or z-axis of the surgical table (e.g., is the base of the computer-assisted device aligned with the surgical table or at an angle relative to the surgical table due to a rotation of the base of the surgical table on the floor and/or a rotation of the base of the computer-assisted device).

According to some embodiments, the registration is determined using one or more physical registration devices that force a known geometric relationship between the surgical table and the patient side cart. In some examples, the physical registration devices may include one or more bars, jigs, and/or the like that lock a position and/or orientation of the patient side cart relative to the surgical table. In some examples, the techniques for registering the surgical table and the computer-assisted device using physical registration devices are described in further detail in PCT Patent Application No. PCT/US2015/20891 entitled "Methods and Devices for Tele-Surgical Table Registration," which was filed Mar. 17, 2015, which is hereby incorporated by reference in its entirety.

According to some embodiments, the geometric relationship of the registration is determined using one or more articulated and/or flexible registration devices that are used to determine a known position and/or orientation between known points on the surgical table and the patient side cart. In some examples, the registration devices may include an articulated structure with one or more sensors for reporting positions and/or orientations of one or more joints of the articulated structure from which a kinematic model of the registration structure may be used to determine a geometric relationship between the two ends of the articulated structure. In some examples, the registration devices may include an optical fiber having a core region with a plurality of fiber Bragg gratings located along the full length of the core. In some examples, an interrogator for the optical fiber may be used to detect bending and twisting of the optical fiber to determine the geometric relationship between the ends of the optical fiber. In some examples, the optical fiber may be used to determine the registration between the surgical table and the computer-assisted device using techniques similar to those described in more detail in U.S. Pat. No. 7,720,322 entitled "Fiber Optic Shape Sensor," which was filed Jun. 30, 2008, which is hereby incorporated by reference in its entirety.

According to some embodiments, the geometric relationship of the registration may be determined based on observing how movement of the surgical table induces motion in the remote centers of motion of the computer-assisted device subject to instrument dragging. In some examples, the movements of the surgical table observed may be associated with surgical table movement that occurs as a result of surgical table movement requests made by an operator, such as by using the movement request buttons 640, and/or by initiating a controlled sequence of surgical table movements by a registration procedure. In some examples, the registration may take place in stages where $\theta_Z$ registration is determined first followed by horizontal or XY registration. In some examples, the XY registration may occur in phases until both tilt and Trendelenburg movements are observed. In some examples, the techniques for registering the surgical table and the computer-assisted device are described in further detail in U.S. Provisional Patent Application No. 62/134,296 entitled "System and Method for Registering to a Surgical Table," which was filed Mar. 17, 2015, and concurrently filed PCT Patent Application No. PCT/US2015/057664 entitled "System and Method for Registering to a Surgical Table" and published as WO2016/069655 A1, both of which are hereby incorporated by reference in their entirety.

At a process 430, surgical table motion is performed to carry out a surgical function. Once intraoperative table motion is entered during process 420 and the disturbances due to the release and/or unlocking of the joints used to permit instrument dragging are compensated for, motion of the surgical table begins. In general, surgical table motion uses an iterative request-check-move procedure whereby surgical table movement requests are received, the requested movement is evaluated to determine whether it should be allowed, and then after receiving approval, the surgical table movement is executed. In this iterative procedure, whether or not the surgical table is allowed to move is controlled by the computer-assisted device so that the surgical table movement is allowed to occur within the ability of the computer-assisted device to appropriately respond and compensate for the surgical table movement while maintaining proper safety for the patient, the surgical table, and/or the computer-assisted device.

Figure 7:
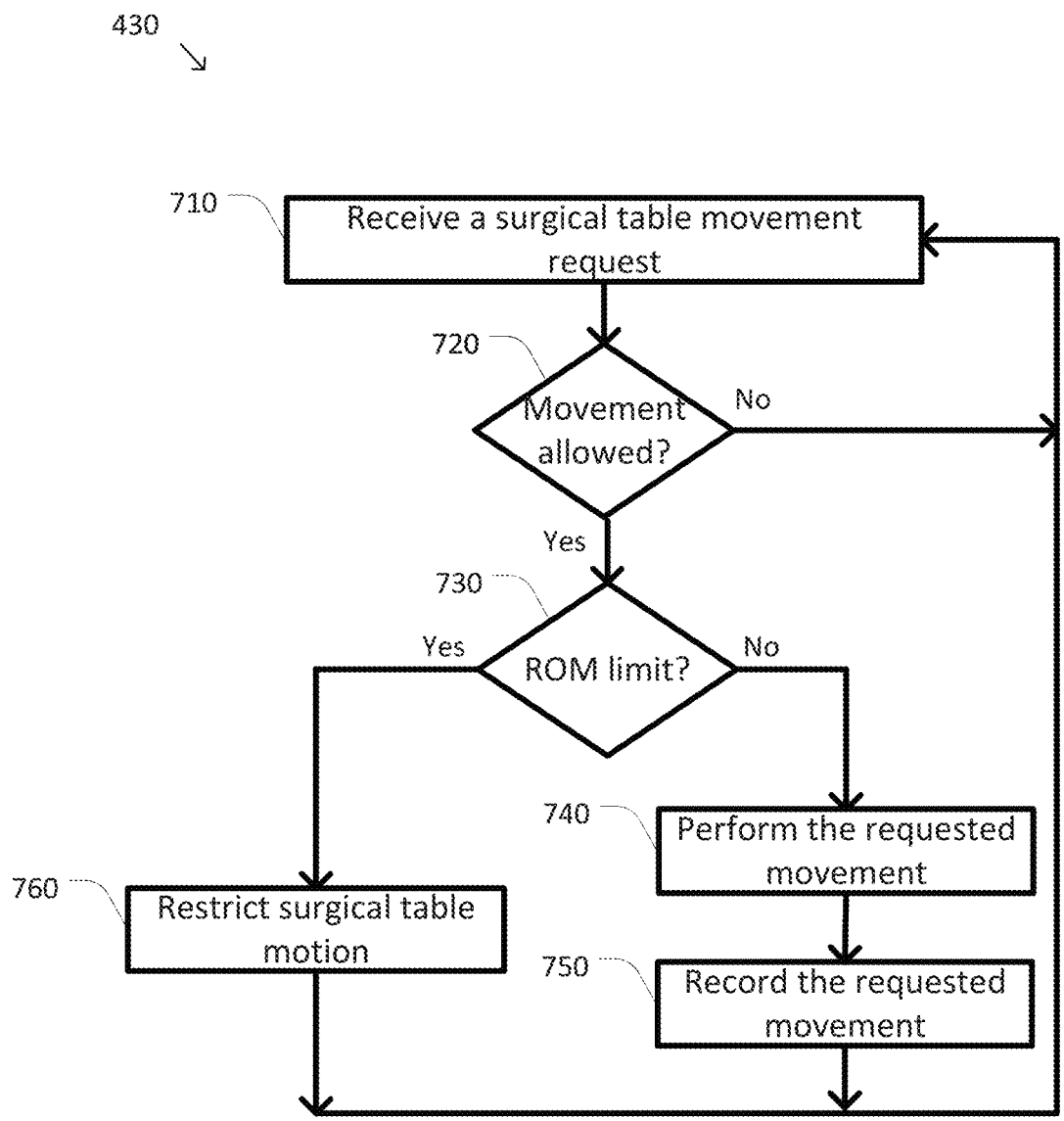
FIG. 7 is a simplified diagram of a process for performing surgical table motion according to some embodiments.

FIG. 7 is a simplified diagram of the process 430 for performing surgical table motion according to some embodiments. One or more of the processes 710-760 of process 430 may be implemented, at least in part, in the form of executable code stored on non-transient, tangible, machine readable media that when run by one or more processors (e.g., the processor(s) 140 in control unit 130) may cause the one or more processors to perform one or more of the processes 710-760. In some embodiments, process 430 may be used to perform the iterative request-check-move procedure. In some examples, the recording of movements during process 430 may optionally be used to support one or more additional surgical table motion modes that move the surgical table away from positions and/or orientations that may not be adequately responded to and/or compensated for by the computer-assisted device.

According to some embodiments, process 430 is performed using a repetitive control loop. In some examples, as each surgical table movement request is received, it is processed as described below using processes 710-760, processes 710-760 are then repeated in rapid succession to give the impression that a continuous stream of surgical table movement requests are being received, approved, and applied. In some examples, as an operator presses and holds down movement request buttons, such as any of the movement request buttons 640, the surgical table movements that are approved appear to be applied for as long as the movement request buttons are held down. In some examples, the repetitive control loop of processes 710-760 is completed multiple times per second, such as every 10 ms (milliseconds). In some examples, once a movement request is approved and the same movement request button is held down, movement of the surgical table is allowed until a range of motion limit, impending collision, an operator stop command, and/or some other event triggers rescission of the approval of the movement request.

At a process 710, a surgical table movement request is received. In some examples, the surgical table movement request may be initiated by a surgeon and/or other medical personnel using an operator workstation, such as the workstation discussed with respect to FIG. 1. In some examples, the surgical table movement request may be initiated by a surgeon and/or other medical personnel, such as an anesthesiologist, using a surgical table command unit, such as surgical table command unit 600. In some examples, the surgical table movement request may correspond to the pressing and holding down of one of the movement request buttons 640. In some examples, the surgical table movement request may be communicated to the control unit of the computer assisted device, such as control unit 130, through one or more communications connections coupling the surgical table command unit to the control unit. In some examples, a surgical table movement request may be initiated by the activation of one or more API calls in the motion control application, such as motion control application 160, for the computer-assisted device.

At a process 720, it is determined whether surgical table movement is allowed. In some embodiments, the determination of whether surgical table movement is allowed may be based on any one or more of the checks used to determine whether intraoperative table motion is allowed during process 415. In some examples, use of the same checks represents ongoing monitoring of the surgical table and the computer-assisted device during intraoperative table motion to insure that proper safety is being maintained for the patient, the surgical table, and/or the computer-assisted device. In some examples, the checks may optionally include one or more of the following: confirming that the feet, wheels, and/or mounting clamps of the surgical table and the computer-assisted device remain locked, confirming that the surgeon and/or other operator is still head-in on the operator console, confirming that the end effectors of the instruments mounted to docked articulated arms are within the field of view of the imaging device and/or withdrawn into a corresponding cannula, confirming that the computer-assisted device is still tracking the on-going surgical table motion, confirming that the computer-assisted device and the surgical table are communicating, and/or the like. In some examples, the one or more checks may further include confirming that a type of movement being requested is permitted during intraoperative table motion. In some examples, the types of movement permitted during intraoperative table motion may be restricted to a subset of possible movements for the surgical table, such as height adjustments, tilt adjustments, Trendelenburg adjustments, and/or slide adjustments. In some examples, the types of movement permitted may be further restricted based on a determination of allowed surgical table movements determined during process 760 as discussed in further detail below. In some examples, the types of movement permitted may also be limited depending upon whether the registration of process 425 has completed. In some examples, when fewer than three articulated arms and/or manipulators are docked to the patient, the types of surgical table motions are restricted to height adjustments due to a restricted ability to adequately determine the registration between the surgical table and the computer-assisted device. When the requested surgical table movement is allowed and/or granted by the computer-assisted device, range of motion (ROM) limits are examined before performing the movement beginning with a process 730. When the surgical table movement request is not allowed, the surgical table movement request is ignored and process 430 continues by waiting for another surgical table movement request using process 710. In some examples, when the surgical table movement request is not allowed, one or more audio and/or visual alerts may be provided to the surgeon at the operator console and/or the medical personnel operating the surgical table command unit.

At the process 730, it is determined whether the computer-assisted device is at or near a range of motion limit. In addition to the checks performed during process 720, the joints in the set-up joints and/or manipulator that are used to compensate for the surgical table movement are monitored to determine whether they are at or near a range of motion limit. When a joint in one of the is at or near a range of motion limit this is an indicator that the corresponding articulated arm may not be able to properly compensate for the motions induced in the instrument and/or the end effector caused by the instrument dragging of the corresponding cannula at the corresponding remote center of motion. In some examples, the range of motion limits include hard range of motion limits due to physical characteristics of the joints that do not permit the joints to move beyond a certain limit. In some examples, the range of motion limits include soft range of motion limits that are set at points before corresponding hard range of motion limits that help stop the movement of joints before they reach the hard range of motion limits. In some examples, the soft range of motion limit may be set a fixed percentage, such as 1, 2, or 5 percent, of the full range of motion for the corresponding joint before the corresponding hard range of motion limit. In some examples, the range of motion limits are applied in a predictive fashion where a current position of a joint and a current velocity of the joint are used to predict that continued similar motion could shortly result in reaching a range of motion limit. When each of the joints of the computer-assisted device are not at or near corresponding range of motion limits, the surgical table movement is performed beginning with a process 740. When one or more of the joints of the computer-assisted device are at or near corresponding range of motion limits, remedial surgical table movement is performed using a process 760. In some examples, when one or more of the joints of the computer-assisted device are at or near corresponding range of motion limits, one or more audio and/or visual alerts may optionally be provided to the surgeon at the operator console and/or the medical personnel operating the surgical table command unit.

At the process 740, the requested surgical table movement is performed. After it is determined that the requested surgical table movement is allowed during process 720 and no range of motion limits for the computer-assisted device are going to interfere with the ability of the computer-assisted device to compensate for the surgical table movement during process 730, the surgical table is allowed to execute the requested surgical table movement. In some examples, the control unit for the computer-assisted device sends one or more messages to the surgical table via, for example, the connection established during process 510. The one or more messages authorize the surgical table to perform the requested surgical table movement. In some examples, the requested surgical table movement is performed by sending commands and/or signals to one or more actuators in the articulated structure, such as articulated structure 290, of the surgical table. As some examples, when the requested surgical table movement is a height adjustment of the top of the surgical table, the one or more actuators that control the height of the top of the surgical table are correspondingly activated, and when the requested surgical table movement is a Trendelenburg adjustment, the one or more actuators that control the Trendelenburg angle of the top of the surgical table about the isocenter are correspondingly activated.

In some examples, the requested surgical table movement may optionally be implemented as corresponding velocity commands to the actuators so that as long as the surgical table movement request button is being held down and the movement request is approved, the one or more actuators moves the top of the surgical table at appropriate velocities. In some examples, the velocities are selected to provide a good compromise between rapidity of surgical table motion as balanced by the ability of the computer-assisted device to compensate for the surgical table motion and/or to allow medical personnel to monitor safe movement of the surgical table, the computer-assisted device relative to the patient, movement of the patient, and/or the like. In some examples, the velocities are limited to less than 3 degrees per second (e.g., 1.5 degrees per second) for tilt and/or Trendelenburg adjustments and/or 1 to 3 cm per second (e.g., 2 cm per second) for height and/or slide adjustments.

At an optional process 750, in order to better support recovery from potential future range of motion limit problems, the requested surgical table movement performed during process 740 is recorded. In some examples, the surgical table movement is recorded in memory, such as memory 150. In some examples, the surgical table movement is recorded in a data structure that records the type of the surgical table movement (e.g., table up, tilt right, Trendelenburg reverse), the distance, duration, and/or velocity of the surgical table movement, and, optionally, a time stamp. In some examples, the data structure may be a stack, doubly-linked list, and/or other data structure that supports at least a last-in-first-out access pattern so the order of the recorded movements may be reversed to undo the recorded movements and back away from a range of motion limit and/or other problem. In some examples, the surgical table movement may be recorded in a log and/or other type of file. Upon recording the surgical table movement, surgical table motion continues by returning to process 710 to receive another surgical table movement request.

At the process 760, the surgical table motion is restricted. When one or more of the joints of the computer-assisted device are at or near corresponding range of motion limits, the computer-assisted device acts to restrict the possible motions that the surgical table may make. Several approaches for this are possible.

In some embodiments, the kinematic models of the surgical table and the computer-assisted device, such as the kinematic models of FIG. 3, may be used to evaluate one or more potential surgical table movements. In some examples, each of the possible surgical table movements, such as height up, height down, tilt left, tilt right, Trendelenburg forward, Trendelenburg reverse, and/or slide, is evaluated in turn to determine whether the possible surgical table movement will move the joints of the computer-assisted device toward or away from a corresponding range of motion limit. In some examples, each possible surgical table movement is projected, using the kinematic models of the surgical table and the computer-assisted device as well as the registration transform between the surgical table and the computer-assisted device, to determine how the possible surgical table movement will affect each of the remote centers of motion. In some examples, the corresponding Jacobian for each of the articulated arms may then be used to determine the relationships between motions of the one or more joints of the articulated arms that are at or near corresponding range of motion limits and the corresponding remote centers of motion. When the projected remote center of motion movements and the Jacobian-predicted movements are consistent with a movement away from the corresponding range of motion limits, the corresponding possible surgical table movement is permitted. When the projected remote center of motion movements and the Jacobian-predicted movements are consistent with a movement toward the corresponding range of motion limits, the corresponding possible surgical table movement is not permitted. In some examples, whether a movement is consistent with a movement toward and/or away from the corresponding range of motion limits is determined by extracting the column from the Jacobian associated with the joint at or near the corresponding range of motion limit and taking a dot product with the projected remote center of motion movement. When the dot product is negative, the projected movement is consistent with a movement toward the corresponding range of motion. In some examples, a configurable threshold for the dot product may be used to determine whether the projected motion should be permitted. In some examples, when the configurable threshold is zero, movements in the joints toward the corresponding range of motion limits are prohibited. In some examples, when the configurable threshold is slightly negative, then small movements toward the corresponding range of motion limit will be permitted. In some examples, a possible surgical table movement may yield a different permit/prohibit decision for different remote centers of motion and corresponding instruments. In some examples, the amount by which the configurable threshold is negative may affect how permissive the evaluation becomes. In some examples, when the possible surgical table movement is prohibited as a result of the evaluation for any of the remote centers of motion, the possible surgical table movement is prohibited. Thus, based on each of the dot product tests, each of the possible surgical table movements may be evaluated to determine whether they should be permitted and/or prohibited.

In some embodiments, the ability to evaluate potential surgical table movements may be limited based on whether and/or to what extent a registration transform between the surgical table and the computer-assisted device, such as registration transform 325, is known. In some examples, when no registration has occurred, the surgical table movements may be limited to height adjustments. In some examples, when both the surgical table and the computer-assisted device have a common vertical up or z-axis, height adjustments in the surgical table may be mapped to vertical movements in the remote centers of motion so that the corresponding range of motion limits that are affected by vertical movements in the remote centers of motion are evaluated to permit and/or prohibit the height adjustments. In some examples, when the XY registration is partial, such as because both tilt and Trendelenburg movements have not been observed during process 425, possible surgical table movements associated with the observed one of tilt and Trendelenburg movements are evaluated and possible surgical table movements associated with the other of the tilt and Trendelenburg movements are prohibited. In some examples, when the possible surgical table movements include Trendelenburg movements that may be limited by a range of motion limit in the slide adjustment of the surgical table, the possible surgical table movements may include Trendelenburg movements both with and without isocentering.

In some embodiments, surgical table movements are restricted based on the history of surgical table movements recorded during process 750. In some examples, surgical table motion are restricted to the reverse of recent movements of the surgical table. By reversing the recent surgical table movements, the patient is moved in a direction opposite to the direction that resulted in the range of motion limit that was detected during process 730. As a result, the remote centers of motion of the instruments reverse their direction, and instrument dragging acts to back the joints of the set-up joints and/or the manipulators away from the range of motion limit. In some embodiments, process 760 is used to implement a "go back the way you came" feature to avoid the range of motion limit. Depending upon the implementation, the reversing of the recorded surgical table movement may be performed in a semi-automated way and/or by recommending surgical table movements to the operator of the surgical table.

In some embodiments, when the semi-automated process is used, one or more of the most recently recorded surgical table movements are applied in reverse. As an example, a recent height up movement of 1 cm/s for 10 ms is reversed as a 1 cm/s height down movement for 10 ms. In some examples, the number of recent surgical table movements to reverse may vary from 1 to 5 (e.g., 2) recorded surgical table movements based on a configurable setting. In some examples, when more than one recent surgical table movement is reversed, they are reversed in the opposite order in which they initially occurred so that the most recent surgical table movement is reversed first, the second most recent surgical table movement is reversed second, and so on. In some examples, as each of the surgical table movements is reversed, the corresponding surgical table movement is removed from the data structure, log, and/or file used to record the requested surgical table movements during process 750. In some examples, when the data structure is a stack, the most recent surgical table movement may be popped off the stack. After the semi-automated reversing is completed, surgical table motion continues by returning to process 710 to await another surgical table movement request.

In some embodiments, the processor may display, to the operator of the surgical table, indications of surgical table movements that are likely to address the range of motion limit. In some examples, the restrictions to the surgical table movements may be used to limit the possible surgical table movement requests that may be made by the operator. For example, when a height up movement resulted in the range of motion limit detected during process 730, the surgical table movement requests may be limited to only height down movement requests. In some examples, as the operator makes movements to move away from a range of motion limit, additional types of surgical table movement requests may be permitted. In some examples, when an operator is using surgical table command unit 600, the permitted surgical table movement requests may be indicated by illuminating the corresponding movement request buttons 460 and removing illumination from the movement request buttons 460 that are not permitted. After the surgical table motion is restricted, surgical table motion continues by returning to process 710 to await another surgical table movement request.

Referring back to FIG. 4, at a process 435 surgical table tracking is performed. As the surgical table motion is being performed during process 430, the patient moves and, along with the patient, the remote centers of motion of the manipulators begin to move. In order to reduce the forces applied by the body wall of the patient to the cannulas located at the remote centers of motion, the computer-assisted device is placed in a surgical table tracking mode in which the remote centers of motion of the manipulators are allowed to move due to instrument dragging. In some examples, one or more joints of the computer-assisted device are allowed to move to adjust to the instrument dragging and to correct for errors in the pose of any of the instruments mounted to the instruments due to the movement of the remote centers of motion.

Figure 8:
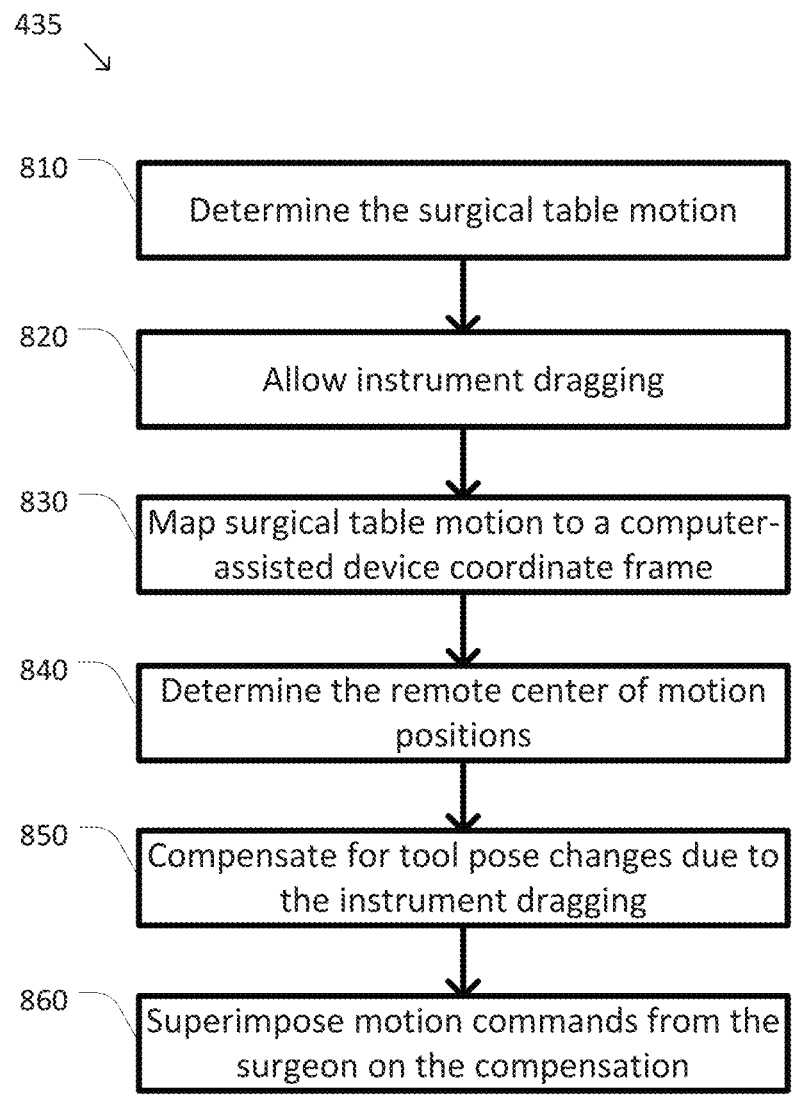
FIG. 8 is a simplified diagram of a process for surgical table tracking according to some embodiments.

FIG. 8 is a simplified diagram of the process 435 for surgical table tracking according to some embodiments. One or more of the processes 810-860 of process 435 may be implemented, at least in part, in the form of executable code stored on non-transient, tangible, machine readable media that when run by one or more processors (e.g., the processor 140 in control unit 130) may cause the one or more processors to perform one or more of the processes 810-860. In some embodiments, process 435 may be used to track the motion of the surgical table and make adjustments in the pose of any instruments to compensate for the motion of the patient induced by the surgical table motion. In some examples, process 860 is optional and may be omitted for instruments that are not being actively controlled by a surgeon.

At a process 810, the surgical table motion is determined. As the surgical table is being moved during process 430 and more particularly during process 740, the motion of the surgical table is monitored. As part of the monitoring, the nature and character of the surgical table motion is determined so that its effects on the patient and/or the remote centers of motion of the instruments are monitored as well. In some examples, the surgical table motion is characterized by using a table base to table top transform, such as table base to table top transform 315. In some examples, the surgical table provides the current table base to table top transform to the computer-assisted device. In some examples, the surgical table provides a difference (delta) between the current table base to table top transform since the last time the table base to table top transform was provided. In some examples, the surgical table provides the current positions and/or velocities of the joints in the articulated structure of the surgical table so that the computer-assisted device is able to determine the current table base to table top transform using one or more kinematic models of the articulated structure of the surgical table. In some examples, the surgical table sends one or more messages to the computer-assisted device to exchange the table base to table top transform, the delta table base to table top transform, the current joint positions, and/or current joint velocities.

At a process 820, as a result of the release and/or unlock of the one or more joints in the set-up joints and/or manipulators during process 420, instrument dragging is allowed. Thus, as the surgical table undergoes the motion determined during process 810, similar motion is expected to occur in the remote center of motion of each of the instruments. As some examples, when the height of the surgical table is adjusted upward, the remote centers of motion of the instruments move upward as well, and when the top of the surgical table is rotated about the isocenter for tilt and/or Trendelenburg adjustments, the remote centers of motion of the instruments similarly rotate about the isocenter.

At a process 830, the surgical table motion is mapped to a computer-assisted device coordinate frame. The surgical table motion determined during process 810 is mapped to a coordinate frame associated with the computer-assisted device so that the computer-assisted device may predict how the surgical table motion is going to affect the motion of the remote centers of motion of the instruments and/or the pose of the instruments. In some examples, the coordinate frame may be a global and/or a local coordinate frame for the computer-assisted surgical device, such as the device base coordinate frame 320, the arm mounting platform coordinate frame 330, and/or the like. In some examples, the surgical table motion, as reflected in the corresponding motion of the remote centers of motion of the instruments, is mapped to the device base coordinate frame of the computer-assisted device by applying a combination of the table base to table top transform and the table base to device base transform. Once the motion of the remote center of motion is mapped to the device base coordinate frame, the motion of the remote center of motion is mapped to a suitable coordinate frame of the computer-assisted device, such as the arm mounting platform coordinate frame 330, any of the manipulator mount coordinate frames 341, 351, and/or 361, any of the remote center of motion coordinate frames 342, 352, and/or 362, etc. of the computer-assisted device using the kinematic models and transforms of the computer-assisted device. In some examples, the mapping of the surgical table motion is used to predict how the remote centers of motion of the instruments may move due to the surgical table motion.

At a process 840, the remote center of motion positions are determined. Because the x-y or horizontal translation between the surgical table and the computer-assisted device may not have been determined during the registration of process 425, the position of the remote centers of motion of the instruments determined during process 830 may not accurately predict the x, y, and z position of each of the remote centers of motion of the instruments. However, in some examples, the x, y, and z position of the remote centers of motion may be alternatively determined using the kinematic models of the computer-assisted device and the joint sensor readings of the computer-assisted device.

At a process 850, the instrument pose changes due to the instrument dragging are compensated for. Using the mapping of the surgical table motion in the coordinate frame of the computer-assisted device from process 830 and the remote center of motion positions determined during process 840, an estimate of how the surgical table motion is moving the remote centers of motion of the instruments is determined. The estimates of the motion of the remote center of motion is then used to estimate how the poses of the instruments are changing due to the surgical table motion using, for example, the remote center of motion to instrument/camera transforms 346, 356, and/or 366. Once an estimate of the instrument pose changes are known, one or more additional joints of the computer-assisted device are driven to compensate for the instrument pose changes so that motion of the instruments and/or end effectors relative to the table top coordinate frame and/or the anatomy of the patient compensates for the surgical table motion.

At an optional process 860, motion commands from the surgeon are superimposed on the compensation. Because one of the goals of intraoperative table motion is to permit control and/or manipulation of the instruments while surgical table motion is taking place, any motion commands for the instruments received from the surgeon, such as via master controls at the operator workstation, are also applied to the instruments and the end effectors. In some examples, the motion commands for the instruments may correspond to relative motions in an endoscopic camera reference frame, such as camera reference frame 363. In some examples, the imaging device, and thus the camera reference frame, may also be controlled to maintain a consistent pose relative to the table top coordinate frame and/or the anatomy of the patient. In some examples, the motion commands are combined with the compensating motions determined during process 850 by superimposing them together. The superimposed motions and are then used to drive the one or more additional joints.

According to some embodiments, and as described above, process 435 and/or processes 810-860 may be performed using various combinations of computer-assisted device transforms and/or coordinate frames depending upon whether the remote center of motion and corresponding instrument is associated with an instrument being actively controlled by a surgeon (and optional process 860 is being performed) and/or associated with an instrument that is not being actively controlled (e.g., the imaging device). In some examples, when surgical table tracking is used for an actively controlled instrument, the techniques as described in greater detail in U.S. Provisional Patent Application No. 62/134,292 entitled "System and Method for Integrating Surgical Table Motion," which was filed Mar. 17, 2015, and concurrently filed PCT Patent Application No. PCT/US2015/057673 entitled "System and Method for Integrated Surgical Table Motion" and published as WO2016/069663 A1, both of which are hereby incorporated by reference in their entirety, may be used to perform process 435 and/or processes 810-860. In some examples, when surgical table tracking is used for an instrument that is not actively controlled, the techniques as described in greater detail in PCT Patent Application No. PCT/US15/21089 entitled "System and Method for Maintaining a Tool Pose," which was filed Mar. 17, 2015, which is hereby incorporated by reference in its entirety, may be used to perform process 435 and/or processes 810-860.

Referring back to FIG. 4, at a process 440, surgical table tracking is monitored. Because of the complexities of intraoperative table motion and the possibility that the computer-assisted device may not be able to adequately compensate for changes in the poses of the instruments, such as during processes 420, 440, and/or 850, the remote centers of motion of the instruments are monitored and/or tracked during intraoperative table motion to ensure that each of the remote centers of motion is moving as expected with the patient. In some examples, when the remote centers of motion are not moving as expected, this condition may indicate that there are increasing forces being applied by the docked cannulas to the body wall of the patient because the remote centers of motion of the instruments being held by the manipulators may be diverging from the body opening points on the patient. In some examples, when these forces are allowed to inappropriately increase, they may result in injury to the patient, damage to the computer-assisted device, and/or damage to the surgical table.

Figure 9:
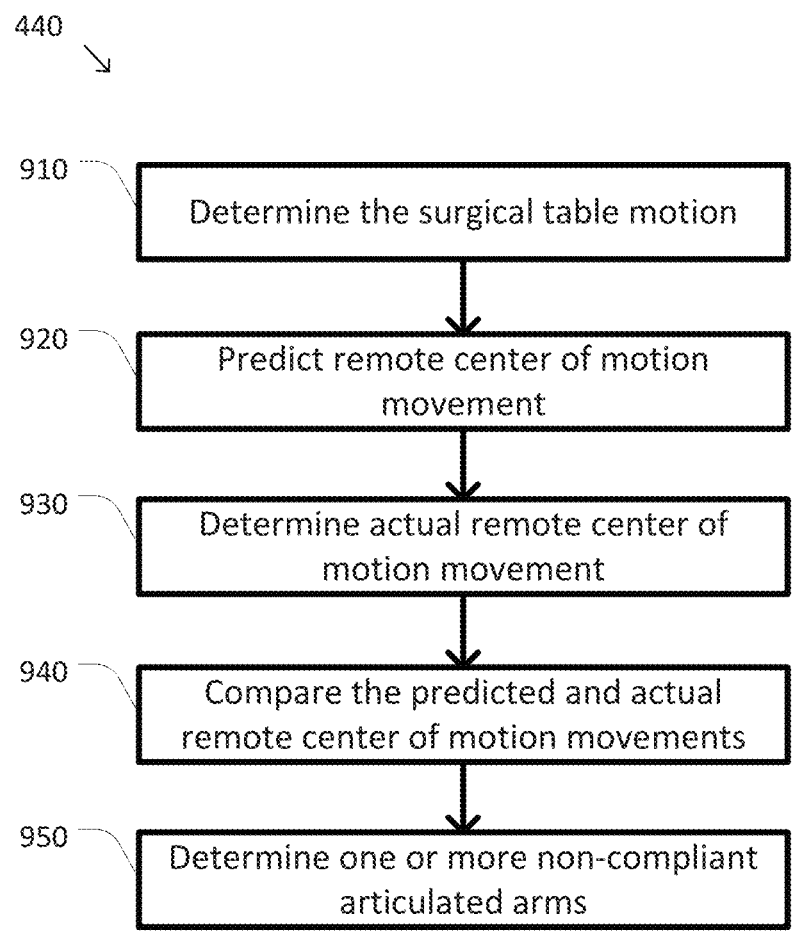
FIG. 9 is a simplified diagram of a process for monitoring surgical table tracking according to some embodiments.

FIG. 9 is a simplified diagram of the process 440 for monitoring surgical table tracking according to some embodiments. One or more of the processes 910-950 of process 440 may be implemented, at least in part, in the form of executable code stored on non-transient, tangible, machine readable media that when run by one or more processors (e.g., the processor 140 in control unit 130) may cause the one or more processors to perform one or more of the processes 810-860. In some embodiments, process 440 may be used to help ensure that the remote centers of motion of the instruments are able to move along with the surgical table motion. In some examples, the remote centers of motion may not be able to move as expected due to obstructions of and/or collisions by the docked articulated arms, undetected range of motion limits, and/or the like.

At a process 910, the surgical table motion is determined. Using process 810 and/or a process substantially similar to process 810, the motion of the surgical table is determined.

At a process 920, remote center of motion movement is predicted. Using the surgical table motion determined during process 910, the table base to table top transform, and the table base to device base transform, the surgical table motion is mapped to the device base coordinate frame using, for example, a process similar to process 830. Once the surgical table motion is mapped to the device base coordinate frame, the kinematic models and/or transforms of the computer-assisted device, such as the device base to arm mounting platform coordinate transform 335, arm mounting platform to manipulator mount transforms 344, 354, and/or 364, and/or the manipulator mount to remote center of motion transforms 345, 355, and/or 365, are used to predict how the surgical table motion will result in movement of the remote centers of motion of the instruments. In some examples, the delta of the table base to table top transform 315 as mapped to the various remote center of motion coordinate frames 342, 352, and/or 362 is used to predict the remote center of motion movement.

At a process, 930, actual remote center of motion movement is determined. Using a process similar to process 840, the actual locations of the remote centers of motion of the manipulators are determined.

At a process 940, the predicted and actual remote center of motion movements are compared. The predicted remote center of motion movements determined during process 920 and the actual remote center of motion movements determined during process 930 are compared to determine whether the remote centers of motion are moving as expected. In some examples, the comparison may include determining whether each of the actual remote center of motion positions is within a suitable error tolerance, such as 12 mm, of the corresponding predicted remote center of motion position. In some examples, the comparison may optionally include determining whether the actual movement of the remote centers of motion maintains one or more geometric relationships among the remote centers of motion, such as relative distances and angular relationships among a constellation defined by the potions of the remote centers of motion in a common coordinate frame.

At a process 950, one or more non-compliant articulated arms are determined. When the comparison of process 940 indicates that one or more of the remote centers of motion is not moving as expected, the differences between the actual and predicted remote center of motion movements are used to determine which of the articulated arms and/or manipulators is not able to comply with and compensate for the surgical table motion. The one or more non-compliant articulated arms may then be communicated to the surgeon and/or medical personnel using one or more audio and/or visual alerts, such as a message displayed on the operator workstation, flashing lights on the non-compliant articulated arms, and/or the like.

According to some embodiments, process 440 and/or processes 910-950 may be performed using the techniques as described in greater detail in U.S. Provisional Patent Application No. 62/134,252 entitled "System and Method for Monitoring Control Points during Reactive Motion," which was filed Mar. 17, 2015, and concurrently filed PCT Patent Application No. PCT/US2015/057670 entitled "System and Method for Monitoring Control Points during Reactive Motion" and published as WO2016/069660 A1, both of which are hereby incorporated by reference in their entirety.

Referring back to FIG. 4, at a process 445, status of the surgical table and the computer-assisted device are displayed. This status display may be useful, such as when the surgeon has to remain head-in at an operator workstation during intraoperative table motion and/or the surgeon is not able to directly observe the surgical table and/or the computer-assisted device. In addition, the patient is typically covered with one or more sterile drapes that often make it difficult to observe and/or assess the orientation of the top of the surgical table. In some examples, a surgeon may use a steeper surgical table angle (e.g., tilt and/or Trendelenburg) than is generally needed in order to ensure a desired gravity retraction occurs, which may add additional stress to the patient and cause injury.

Figure 10:
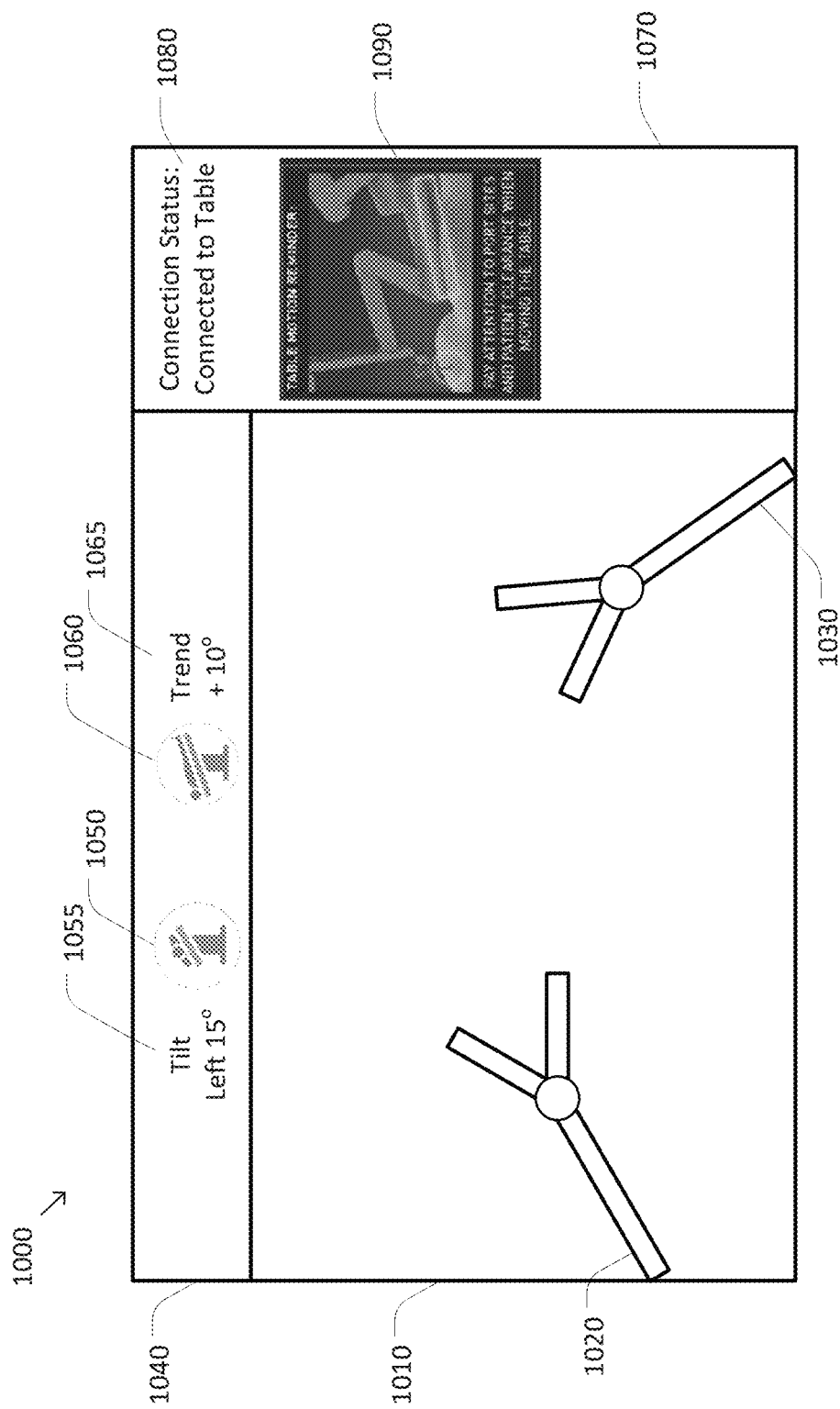
FIG. 10 is a simplified diagram of a user interface according to some embodiments.

FIG. 10 is a simplified diagram of a user interface 1000 according to some embodiments. In some embodiments, user interface 1000 may be displayed at the operator workstation, at a display located on or near the surgical table, and/or the like. As shown in FIG. 10, user interface 1000 provides status information for one or more medical personnel involved with a surgery and/or other procedure. User interface 1000 is divided into several regions for displaying different types of information to the medical personnel. In some examples, different regions and/or different arrangement of the regions may be used depending upon where and/or to which medical personnel user interface 1000 is displayed. Although not shown in FIG. 10, user interface 1000 may be representative of either a left eye or right eye user interface display when the display on which user interface 1000 is displayed is configured for stereoscopic vision, such as when user interface 1000 is displayed on a stereoscopic operator workstation.

A main display region 1010 is used to display live images provided by the imaging device docked to the patient during process 550. In some examples, the live images are images of the interior anatomy of the patient in the vicinity of the desired surgical site. In some examples, the position and/or orientation of the imaging device may be changed by the surgeon using processes that are not further described herein. Shown within the image displayed in the main display region 1010 are two instruments 1020 and 1030, which are shown, for representational purposes only, as instruments having gripper-type end effectors. As the surgeon manipulates instruments 1020 and 1030 using master controls at the operator workstation, the surgeon is able to observe how the instruments 1020 and 1030 are moving during the surgical procedure. In some examples, instruments 1020 and 1030 have to remain within the view of the imaging device during intraoperative table motion, as described during process 415, so that the surgeon may continue to observe instruments 1020 and 1030 throughout intraoperative table motion for any possible complications.

A surgical table status region 1040 is shown located above the main display region 1010, although one of ordinary skill would understand that surgical table status region 1040 may be located elsewhere within user interface, including possibly superimposed on the main display region 1010. Located within the surgical table status region 1040 are several icons and textual fields providing information on the status of the surgical table. As shown, a tilt status icon 1050 is used to indicate the current tilt setting for the surgical table. In some examples, the actual tilt of the surgical table and patient depicted within the tilt status icon 1050 may be adjusted to more accurately depict the tilt of the surgical table. For example, as the surgical table is tilted towards level, the table top and patient within the tilt status icon 1050 may tilt toward level as well. In this way, the surgeon gets a visual depiction of how the surgical table is actually tilted. In some examples, the tilt status icon 1050 may also include one or more visual cues indicating that the tilt of the surgical table is being adjusted. In some examples, the visual cues may include changing the color of the tilt status icon 1050, flashing the tilt status icon 1050, and/or adding clockwise and/or counter-clockwise arrows showing the direction of changing tilt. In some examples, tilt status icon 1050 may be adjusted to reflect an orientation of the patient, such as the patient being placed on the patient's left or right side rather than on the patient's back. In some examples, tilt status icon 1050 may also include one or more visual indicators of a range of motion and/or an extreme orientation limit for the tilt of the table top and/or when the current tilt of the table top is reaching the range of motion and/or extreme orientation limit. In some examples, the range of motion and/or extreme orientation limit may be depicted using a maximum angle line. In some examples, a highlight, such as flashing, color changes, and/or the like, may be used to indicate that the tilt is approaching the range of motion and/or extreme orientation limit. Located next to the tilt status icon 1050 is a tilt value indicator 1055 used to report the current tilt angle and direction of the surgical table.

Also shown is a Trendelenburg status icon 1060 used to indicate the current Trendelenburg setting for the surgical table. In some examples, the actual Trendelenburg orientation of the surgical table and patient depicted within the Trendelenburg status icon 1060 may be adjusted to more accurately depict the Trendelenburg orientation of the surgical table. For example, as the Trendelenburg setting for the surgical table is adjusted towards level, the table top and patient within the Trendelenburg status icon 1060 may move toward level as well. In this way, the surgeon gets a visual depiction of the Trendelenburg orientation of the surgical table. In some examples, the Trendelenburg status icon 1060 may also include one or more visual cues indicating that the Trendelenburg orientation of the surgical table is being adjusted. In some examples, the visual cues may include changing the color of the Trendelenburg status icon 1060, flashing the Trendelenburg status icon 1060, and/or adding clockwise and/or counter-clockwise arrows showing the direction of changing the Trendelenburg orientation. In some examples, Trendelenburg status icon 1060 may be adjusted to reflect an orientation of the patient, such as the patient being placed on the patient's left or right side rather than on the patient's back. In some examples, Trendelenburg status icon 1060 may also include one or more visual indicators of a range of motion and/or an extreme orientation limit for the Trendelenburg setting of the table top and/or when the current Trendelenburg setting of the table top is reaching the range of motion and/or extreme orientation limit. In some examples, the range of motion and/or extreme orientation limit may be depicted using a maximum angle line. In some examples, a highlight, such as flashing, color changes, and/or the like, may be used to indicate that the Trendelenburg setting is approaching the range of motion and/or extreme orientation limit. Located next to the Trendelenburg status icon 1060 is a Trendelenburg value indicator 1065 used to report the current Trendelenburg orientation angle of the surgical table.

In some embodiments, use of the tilt status icon 1050 and/or the Trendelenburg status icon 1060 provides a useful and intuitive table orientation readout for the surgeon and/or medical personnel. In some examples, the tilt status icon 1050 and/or the Trendelenburg status icon 1060 aids the surgeon in determining an effective amount of surgical table orientation to support a particular procedure as the surgeon is able to simultaneously monitor the orientation of the top of the surgical table while also observing how the patient's anatomy is responding in the main display region 1010. In some examples, the tilt status icon 1050 and/or the Trendelenburg status icon 1060 may improve repeatability of surgical table orientations used to support various procedures. In some examples, the tilt status icon 1050 and/or the Trendelenburg status icon 1060 may allow the surgeon to better moderate the amount of tilt and/or Trendelenburg orientation used during a procedure. In some examples, the tilt status icon 1050 and/or the Trendelenburg status icon 1060 may aid the surgeon in recognizing when substantially steeper tilt and/or Trendelenburg orientations are present and/or when tilt and/or Trendelenburg orientations that are steeper than are conventionally used during procedures. In some examples, the highlighting of the extreme orientation limits may further avoid undesirably and/or unnecessarily steep tilt and/or Trendelenburg orientations. Over time, surgeons may learn approximate minimum orientations needed to achieve a desired effect, and so limit patient stress.

In some examples, the presence of the tilt status icon 1050 and/or the Trendelenburg status icon 1060 may further indicate that a communication connection is established between the surgical table and the computer-assisted device. In some examples, the tilt status icon and/or the Trendelenburg status icon 1060 may be removed by user interface 1000 when the communication connection is not established between the surgical table and the computer-assisted device, when integrated table motion is not permitted, and/or the like. And, an optional indication that the status icons 1050 and 1060 are not present may be included in interface 1000.

Although not shown in FIG. 10, surgical table status region 1040 may include additional status icons and/or indicators. In some examples, the additional status icons and/or indicators may indicate height and/or slide settings for the surgical table, how the patient is placed on the surgical table, whether intraoperative table motion has been entered, whether the feet and/or wheels of the surgical table and/or the computer-assisted device are locked, and/or the like.

User interface 1000 may also include an optional informational message region 1070. Informational message region 1070 may be used to display one or more informational messages that are applicable to intraoperative table motion. Two representative informational messages are currently shown in FIG. 10, although one of ordinary skill would understand that fewer or more informational messages may be displayed as appropriate. A connection status informational message 1080 shows the connection status between the surgical table and the computer-assisted device. In some examples, the connection status may be related to the connection established during process 510. An alert-type informational message 1090 is providing a warning to the surgeon that it may be desirable to monitor clearance between the patient and the articulated arms and/or manipulators before proceeding with intraoperative table motion. In some examples, additional informational messages, such as notifications of denied entry into intraoperative table motion during process 415, range of motion limits detected during process 730, non-compliant articulated arms detected during process 950, and/or the like may be displayed in informational message region 1070.

As discussed above and further emphasized here, FIG. 10 is merely an example which should not unduly limit the scope of the claims. One of ordinary skill in the art would recognize many variations, alternatives, and modifications. According to some embodiments, one or more additional display regions may show live top and/or side views of the surgical table, patient, and/or computer-assisted device.

Referring back to FIG. 4, at a process 450, intraoperative table motion is exited. As the surgical table and the computer-assisted device are being operated in intraoperative table motion, checks are made to determine whether intraoperative table motion should be continued or exited. In some examples, intraoperative table motion may be exited based on a command issued by the surgeon using the operator workstation, medical personnel pressing the intraoperative table motion entry button 610 on the surgical table command unit 600, and/or the like. In some examples, any of several safety interlocks may result in termination of intraoperative table motion. In some examples, intraoperative table motion may be exited when the connection between the surgical table and the computer-assisted device established during process 510 is lost, when the feet, wheels, and/or mounting clamps of either the surgical table or the computer-assisted device are unlocked, when cannula are attached and/or detached from a manipulator, when it is determined that the surgeon is no longer head-in at the operator workstation, when the end effectors of the instruments mounted to the instruments are no longer within the field of view of the imaging device docked during process 550 and not retracted into a respective cannula, when any joint unlocking buttons on any of the articulated arms and/or manipulators are pressed, and when any other potentially unsafe condition is detected. In some examples, intraoperative table motion may be exited as a result of a range of motion limit detected during process 730 that is not resolved, when one or more non-compliant articulated arms are detected during process 950, and/or the like. In some examples, one or more power and/or system faults in the surgical table and/or the computer-assisted device may also result in intraoperative table motion exit.

As discussed above and further emphasized here, FIG. 4 is merely an example which should not unduly limit the scope of the claims. One of ordinary skill in the art would recognize many variations, alternatives, and modifications. According to some embodiments, one or more of the processes 405-450 may be performed in different orders than the order implied in FIG. 4. In some examples, one or more of the process 425-445 may be performed in any order and/or partially or totally in parallel.

Some examples of control units, such as control unit 130 may include non-transient, tangible, machine readable media that include executable code that when run by one or more processors (e.g., processor 140) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

We claim:

1. A device comprising:
    an articulated arm having one or more joints and a distal portion distal to the one or more joints; and
    a control unit coupled to the one or more joints;
    wherein, to support integrated motion with a separate table communicatively coupled to the device via a communications connection, the control unit is configured to:
        receive a table movement request from the table;
        determine whether allowing the table movement request would result in a first joint of the one or more joints being at a range of motion limit;
        allow the table to perform the table movement request based on determining that allowing the table to perform the table movement request would not result in the first joint being at the range of motion limit;
        track movement of the table due to performing the table movement request; and
        maintain, using the one or more joints and based on the tracked movement of the table, a position, an orientation, or both the position and orientation of the distal portion relative to the table.

2. The device of claim 1, wherein to allow the table movement request, the control unit is further configured to allow the table movement request in response to determining that none of the one or more joints are at a corresponding range of motion limit.

3. The device of claim 1, wherein the control unit maintains the position, the orientation, or the position and the orientation while the table performs the table movement request.

4. The device of claim 1, wherein when the first joint is determined to be at the range of motion limit, the control unit further prohibits further allowance of table movement requests until the first joint is no longer at the range of motion limit.

5. The device of claim 1 wherein when the first joint is determined to be at the range of motion limit, the control unit is further configured to direct the table to reverse one or more previously performed table movements.

6. The device of claim 1, wherein when the first joint is determined to be at the range of motion limit, the control unit is further configured to restrict types of table movement requests that are allowed.

7. The device of claim 6, wherein the control unit is further configured to restrict the types of table movement requests that are allowed based on a record of previous table movement requests that were allowed.

8. The device of claim 6, wherein to restrict the types of table movement requests that are allowed, the control unit is further configured to prohibit the table movement request where performing the table movement request would result in motion of the first joint toward or past the range of motion limit.

9. The device of claim 1, wherein:
the one or more joints comprise one or more second joints and one or more third joints;
to maintain the position, the orientation, or both the position and the orientation, the control unit is configured to:
use the one or more second joints to allow the articulated arm to track the movement of the table due to performing the table movement request; and
compensate for changes in the position, the orientation, or both the position and orientation of the distal portion relative to the table due to the tracked movement of the table by performing compensating motions in the one or more third joints.

10. The device of claim 1, wherein the control unit is further configured to:
receive motion commands from an operator; and
superimpose the motion commands on motions of the one or more joints used to maintain the position, the orientation, or both the position and orientation of the distal portion relative to the table.

11. A method comprising:
receiving, by a control unit of a device, a table movement request from a separate table communicatively coupled to the device via a communication connection;
determining, by the control unit, whether allowing the table to perform the table movement request would result in a first joint of one or more joints of the device being at a range of motion limit;
allowing, by the control unit, the table to perform the table movement request based on determining that allowing the table movement request would not result in the first joint being at the range of motion limit;
tracking, by the control unit, movement of the table due to performing the table movement request; and
maintaining, by the control unit using the one or more joints and based on the tracked movement of the table, a position, an orientation, or both the position and orientation of a distal portion of the device relative to the table, the distal portion being distal to the one or more joints.

12. The method of claim 11, wherein allowing the table movement request comprises allowing the table movement request in response to determining that none of the one or more joints are at a corresponding range of motion limit.

13. The method of claim 11, wherein maintaining the position, the orientation, or the position and the orientation is performed while the table performs the table movement request.

14. The method of claim 11 further comprising when the first joint is determined to be at the range of motion limit, directing the table to reverse one or more previously performed table movements.

15. The method of claim 11, further comprising when the first joint is determined to be at the range of motion limit, prohibiting the table movement request where performing the table movement request would result in motion of the first joint toward or past the range of motion limit.

16. The method of claim 11, further comprising:
receiving motion commands from an operator; and
superimposing the motion commands on motions of the one or more joints used to maintain the position, the orientation, or both the position and orientation of the distal portion relative to the table.

17. A non-transitory machine-readable medium comprising a plurality of machine-readable instructions which when executed by one or more processors associated with a device are adapted to cause the one or more processors to perform a method comprising:
receiving a table movement request from a separate table communicatively coupled to the device via a communication connection;
determining whether allowing the table to perform the table movement request would result in a first joint of one or more joints of the device being at a range of motion limit;
allowing the table to perform the table movement request based on determining that allowing the table movement request would not result in the first joint being at the range of motion limit;
tracking movement of the table due to performing the table movement request; and
maintaining, using the one or more joints and based on the tracked movement of the table, a position, an orientation, or both the position and orientation of a distal portion of the device relative to the table, the distal portion being distal to the one or more joints.

18. The non-transitory machine-readable medium of claim 17, wherein allowing the table movement request comprises allowing the table movement request in response to determining that none of the one or more joints are at a corresponding range of motion limit.

19. The non-transitory machine-readable medium of claim 17, wherein maintaining the position, the orientation, or the position and the orientation is performed while the table performs the table movement request.

20. The non-transitory machine-readable medium of claim 17, wherein the method further comprises:
receiving motion commands from an operator; and
superimposing the motion commands on motions of the one or more joints used to maintain the position, the orientation, or both the position and orientation of the distal portion relative to the table.

* * * * *

UNITED STATES PATENT AND TRADEMARK OFFICE
CERTIFICATE OF CORRECTION

PATENT NO. : 10,993,772 B2
APPLICATION NO. : 16/242750
DATED : May 4, 2021
INVENTOR(S) : Brandon D. Itkowitz et al.

Page 1 of 1

It is certified that error appears in the above-identified patent and that said Letters Patent is hereby corrected as shown below:

On the Title Page

(63) Related U.S. Application Data:
Please delete "Continuation of application No. 15/522,169, filed as application No. PCT/US2015/057656 on Oct. 27, 2015, now Pat. No. 10,226,306." and insert --Continuation of application No. 15/522,169, filed on Apr. 26, 2017, now Pat. No. 10,226,306, which is a 371 of application No. PCT/US2015/057656, filed on Oct. 27, 2015.--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*